(12) United States Patent
Komatsu et al.

(10) Patent No.: US 8,716,531 B2
(45) Date of Patent: *May 6, 2014

(54) METHOD FOR PRODUCING NORBORNENE DERIVATIVE

(75) Inventors: Shinichi Komatsu, Yokohama (JP); Hisashi Sone, Yokohama (JP); Takeshi Koike, Yokohama (JP); Sayako Kawahama, Yokohama (JP)

(73) Assignee: JX Nippon Oil & Energy Corporation, Tokyo (JP)

( * ) Notice: Subject to any disclaimer, the term of this patent is extended or adjusted under 35 U.S.C. 154(b) by 206 days.

This patent is subject to a terminal disclaimer.

(21) Appl. No.: 13/379,133

(22) PCT Filed: May 13, 2010

(86) PCT No.: PCT/JP2010/058133
§ 371 (c)(1),
(2), (4) Date: Dec. 19, 2011

(87) PCT Pub. No.: WO2010/146951
PCT Pub. Date: Dec. 23, 2010

(65) Prior Publication Data
US 2012/0108851 A1 May 3, 2012

(30) Foreign Application Priority Data

Jun. 19, 2009 (JP) ................................. 2009-146803

(51) Int. Cl.
*C07C 45/61* (2006.01)
*C07C 49/653* (2006.01)

(52) U.S. Cl.
USPC .......................... 568/351; 568/376; 568/317

(58) Field of Classification Search
USPC ......................................... 568/317, 351, 376
See application file for complete search history.

(56) References Cited

FOREIGN PATENT DOCUMENTS

| JP | 2006-189474 A1 | 7/2006 |
| JP | 2008-007733 A1 | 1/2008 |

OTHER PUBLICATIONS

Brugidou et al., Condensation diénique des bases de Mannich des cétones, Bulletin de la Societe Chimique de France, pp. 1693-1698 (1966).
Skumov et al., Synthesis of Bi and Tricyclic Spiro Compounds on the Basis of Alloocimene and Cyclopentadiene, Russian Journal of Organic Chemistry, vol. 35, No. 9, pp. 1301-1307 (1999) (translated frm Zhurnal Organisheskoi Khimi, vol. 35, No. 9, 1999, pp. 1332-1338).
Stetter et al., Addition von Aldehyden an cyclishe α-Methyleneketone, Chem. Ber. vol. 117, pp. 682-693 (1984).
International Search Report issued in PCT/JP2010/058133, Jul. 27, 2010.
International Preliminary Report on Patentability issued in International Application PCT/JP2010/058133 (with translation), Jan. 17, 2012.
International Search Report issued Jul. 27, 2010, corresponding with International Application PCT/JP2010/058133.
M. Ya. Skumov et al., "Synthesis of Bi- and Tricyclic Spiro Compounds on the Basic of Alloocimene and Cyclopentadiene", Russian Journal of Organic Chemistry, vol. 35, No. 9, 1999, pp. 1301-1307.

*Primary Examiner* — Sikarl Witherspoon
(74) *Attorney, Agent, or Firm* — Fitch, Even, Tabin & Flannery LLP

(57) ABSTRACT

A method for producing a norbornene derivative includes forming a Mannich base represented by any of general formulae (5) to (7) by reacting a carbonyl compound represented by any of general formulae (1) to (3) and an amine compound represented by general formula (4) with each other in an acidic solvent, to thereby obtain a reaction liquid comprising the Mannich base in the acidic solvent, wherein the acidic solvent comprises a formaldehyde derivative and 0.01 mol/L or more of an acid represented by formula HX; reacting the Mannich base and a diene compound represented by general formula (8) with each other by adding an organic solvent, a base in an amount of 1.0 to 20.0 equivalents to the acid, and the diene compound to the reaction liquid, and then heating the reaction liquid, to thereby form the norbornene derivative represented by any of general formulae (9) to (11).

10 Claims, 4 Drawing Sheets

METHOD FOR PRODUCING NORBORNENE DERIVATIVE

CROSS-REFERENCE TO RELATED APPLICATIONS

This is a U.S. National Phase of International Application PCT/JP2010/058133, filed May 13, 2010, and claims the benefit of foreign priority from Japanese Patent Application 2009-146803, filed Jun. 19, 2009, the entire disclosures of which applications are hereby incorporated herein by reference.

TECHNICAL FIELD

The present invention relates to a method for producing a norbornene derivative.

BACKGROUND ART

Cyclic olefin-based polymers produced by using cyclic olefins as monomers have alicyclic structures in their main chain skeletons. Hence, such a cyclic olefin-based polymer is more likely to be amorphous, exhibits an excellent transparency and heat resistance, has a small photo-elastic coefficient, and also has such properties as a low water absorbing property, acid resistance, alkaline resistance, and a high electrical insulation property. For this reason, use of the cyclic olefin-based polymers has been examined in applications such as display applications (retardation films, diffusion films, liquid-crystal substrates, films for touch panels, light guide plates, protection films for polarizing plates, and the like), optical lens applications, optical disk applications (CD, MD, CD-R, DVD, and the like), optical fiber applications, optical film/sheet applications, and sealing applications for optical semiconductors. Of such cyclic olefin-based polymers, hydrogenated products of cyclic olefin-based polymers obtained by ring opening metathesis polymerization of norbornene derivatives are particularly known to exhibit excellent transparency and heat resistance, and to have a characteristic of a small photo-elastic constant. Hence, such a hydrogenated product, as well as polycarbonate, has been used for retardation films for liquid crystal displays (LCD) and the like. For this reason, development of cyclic olefin-based polymers obtained by using norbornene derivatives has been actively conducted. Under such circumstances, cyclic olefin-based polymers having various structures have been developed. In particular, cyclic olefin-based polymers having a spiro structure, which is one of the cardo structures, and the like have attracted attention, because desired birefringence and wavelength dependence, which are required for retardation films for LCDs, can be controlled freely.

As a method for producing a norbornene derivative having a specific structure such as the spiro-type structure, for example, Japanese Unexamined Patent Application Publication No. 2006-189474 (PTL 1) discloses a method for producing a norbornene derivative having a spiro-type structure, comprising carrying out a Diels-Alder reaction of a vinyl ketone synthesized by a Mannich reaction or the like with cyclopentadiene (Total yield: 53%). Meanwhile, Japanese Unexamined Patent Application Publication No. 2008-7733 (PTL 2) discloses a method for producing a norbornene derivative having a spiro-type structure by utilizing a Diels-Alder addition reaction of cyclopentadiene with an olefin compound (the yield of the vinyl ketone is not shown). In addition, Bulletin de la Societe Chimique de France (5) published in 1966, pages 1693 to 1698 (NPL 1) discloses a method for producing a norbornene having a spiro-type structure, comprising: synthesizing a Mannich base (N,N-dimethylamino methyl-α-tetralone) (yield: 65%) by reacting α-tetralone, which is a cyclic ketone, and dimethylamine hydrochloride in a 35% aqueous formalin solution; and then reacting the Mannich base with cyclopentadiene. Furthermore, Chem. Ber. vol. 117 published in 1984, pages 682 to 693 (NPL 2) discloses a method for producing a norbornene derivative having a spiro-type structure, comprising: synthesizing a Mannich base from a cyclic ketone such as cyclopentanone, cyclohexanone, 1-indanone, or 1-benzosuberone in a usual manner; and then reacting the Mannich base and cyclopentadiene. However, none of the conventional methods for producing a norbornene derivative described in PTLs 1 and 2 and NPLs 1 and 2 is necessarily sufficient from the viewpoint of producing the norbornene derivative in a sufficient yield.

CITATION LIST

Patent Literature

[PTL 1] Japanese Unexamined Patent Application Publication No. 2006-189474
[PTL 2] Japanese Unexamined Patent Application Publication No. 2008-7733

Non Patent Literature

[NPL 1] Bulletin de la Societe Chimique de France (5), published in 1966, pages 1693 to 1698
[NPL 2] Chem. Ber., published in 1984, vol. 117, pages 682 to 693

SUMMARY OF INVENTION

Technical Problem

The present invention has been made in view of the above described problem of the conventional technologies, and an object of the present invention is to provide a method for producing a norbornene derivative, which makes it possible to produce a norbornene derivative having a predetermined structure such as a spiro-type norbornene derivative in a sufficiently high yield.

Solution to Problem

The present inventors have conducted earnest study to achieve the above-described object, and obtained the following results. Specifically, the present inventors first examined the reasons why the above-described conventional technologies are not capable of producing a norbornene derivative in a sufficient yield, and have found that one of the reasons is as follows. Specifically, a vinyl ketone used as a raw material for producing a spiro norbornene undergoes spontaneous dimerization by a hetero Diels-Alder reaction under a temperature condition of 5° C. or above as described in the following reaction formula:

[Chem. 1]

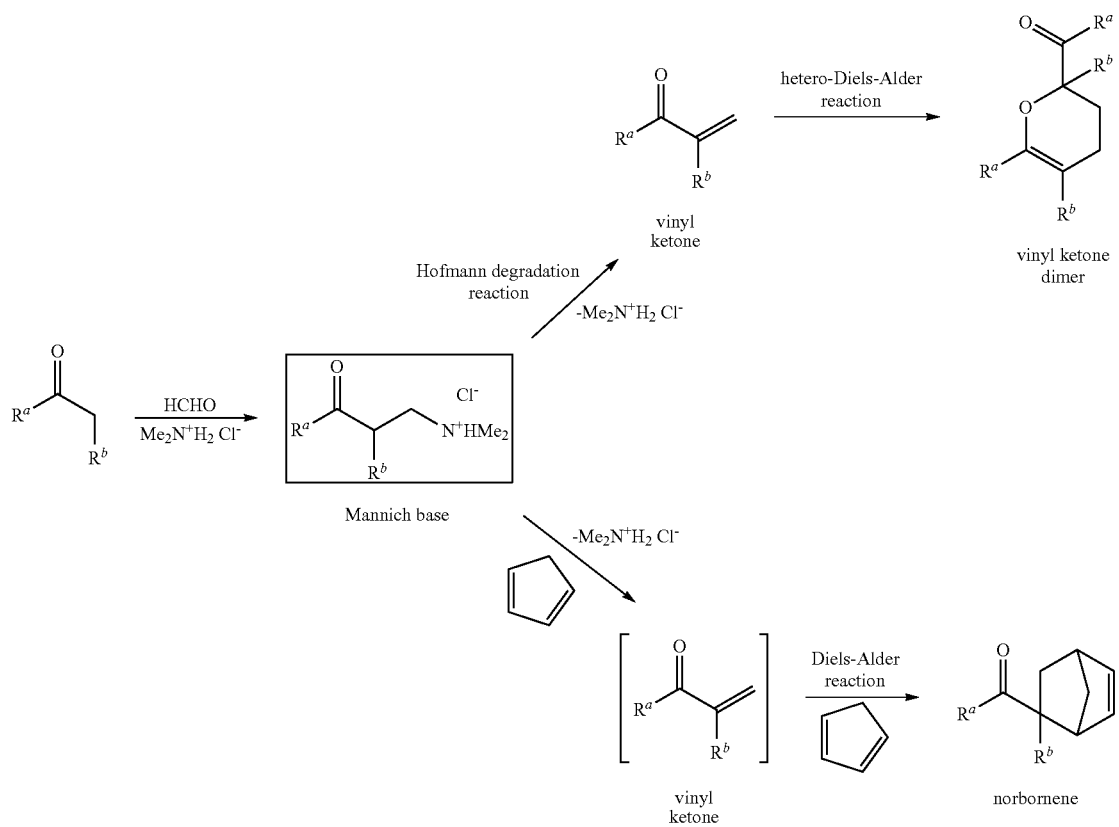

[in the reaction formula, $R^a$ and $R^b$ represent hydrocarbon groups or the like]. Hence, the dimerization of the vinyl ketone proceeds in parallel under an ordinary condition, and thus a vinyl ketone dimer is easily formed. As a result, the yield is lowered due to the dimer formation in the stage of synthesizing the vinyl ketone. Moreover, the present inventors have found that another of the reasons is as follows. Specifically, in the conventional method in which a spiro norbornene is synthesized by preparing a Mannich base as a precursor of a vinyl ketone, isolating the Mannich base, and then subjecting the isolated Mannich base to the Hofmann degradation in the presence of a diene, to thereby generate the vinyl ketone in situ and simultaneously carry out a Diels-Alder reaction, the Mannich base is difficult to utilize sufficiently because of the following reason. Specifically, although the by-production of the vinyl ketone dimer can be suppressed sufficiently, the isolated yield of the Mannich base itself is low, because the Mannich base is an ammonium salt and has a low crystallinity and a high water-solubility. Then, on the basis of the knowledge, the present inventors have further conducted earnest study to achieve the above object. As a result, the present inventors have found that a predetermined norbornene derivative represented by any of the following general formulae (9) to (11) can be produced in a sufficient yield as follows. Specifically, in an acidic solvent, a predetermined carbonyl compound represented by any of the following general formulae (1) to (3) and a predetermined amine compound represented by the following general formula (4) are reacted with each other to form a predetermined Mannich base represented by any of the following general formulae (5) to (7). Here, the acidic solvent comprises a formaldehyde derivative and 0.01 mol/L or more of an acid represented by a formula: HX (in the formula, X represents any selected from the group consisting of F, Cl, Br, I, $CH_3COO$, $CF_3COO$, $CH_3SO_3$, $CF_3SO_3$, $C_6H_5SO_3$, $CH_3C_6H_4SO_3$, $HOSO_3$, and $H_2PO_4$). Thus, a reaction liquid comprising the Mannich base in the acidic solvent is produced. After that, without isolating the Mannich base from the reaction liquid, an organic solvent, a base in an amount of 1.0 to 20.0 equivalents to the acid, and a diene compound represented by the following general formula (8) are added to the reaction liquid, and the mixture is heated. Thus, the Mannich base and the diene compound are reacted to produce the predetermined norbornene derivative. These findings have lead to the completion of the present invention.

Specifically, a method for producing a norbornene derivative of the present invention is a method for producing a norbornene derivative, comprising:

a first step of forming a Mannich base by reacting a carbonyl compound and an amine compound with each other in an acidic solvent, to thereby obtain a reaction liquid comprising the Mannich base in the acidic solvent, the acidic solvent comprising a formaldehyde derivative and 0.01 mol/L or more of an acid represented by a formula: HX (in the formula, X represents any selected from the group consisting of F, Cl, Br, I, $CH_3COO$, $CF_3COO$, $CH_3SO_3$, $CF_3SO_3$, $C_6H_5SO_3$, $CH_3C_6H_4SO_3$, $HOSO_3$, and $H_2PO_4$), the carbonyl compound being represented by any of the following general formulae (1) to (3):

[Chem. 2]

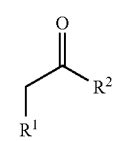
(1)

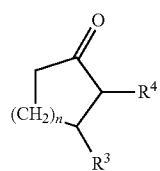
(2)

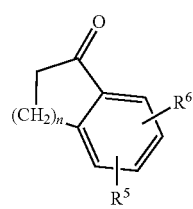
(3)

[in the formulae (1) to (3), $R^1$, $R^2$, $R^3$, $R^4$, $R^5$, and $R^6$ each independently represent any one selected from the group consisting of a hydrogen atom, linear chain saturated hydrocarbon groups having 1 to 10 carbon atoms, branched chain saturated hydrocarbon groups having 3 to 10 carbon atoms, saturated cyclic hydrocarbon groups having 3 to 8 carbon atoms, aryl groups having 6 to 12 carbon atoms, aralkyl groups having 7 to 13 carbon atoms, alkoxy groups having 1 to 10 carbon atoms, a fluorine atom, a chlorine atom, and a bromine atom, and n represents an integer of any of 0 to 4], the amine compound being represented by the following general formula (4):

[Chem. 3]

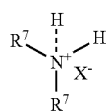
(4)

[in the formula (4), $R^7$s each independently represent any one selected from the group consisting of linear chain saturated hydrocarbon groups having 1 to 20 carbon atoms, branched chain saturated hydrocarbon groups having 3 to 20 carbon atoms, saturated cyclic hydrocarbon groups having 3 to 20 carbon atoms, saturated hydrocarbon groups having a hydroxyl group and 1 to 10 carbon atoms, the two $R^7$s may be bonded to each other to form any one ring selected from the group consisting of a pyrrolidine ring, a piperidine ring, a piperazine ring, and a morpholine ring, and $X^-$ represents any one selected from the group consisting of $F^-$, $Cl^-$, $Br^-$, $I^-$, $CH_3COO^-$, $CF_3COO^-$, $CH_3SO_3^-$, $CF_3SO_3^-$, $C_6H_5SO_3^-$, $CH_3C_6H_4SO_3^-$, $HOSO_3^-$, and $H_2PO_4^-$], the Mannich base being represented by any of the following general formulae (5) to (7):

[Chem. 4]

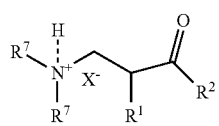
(5)

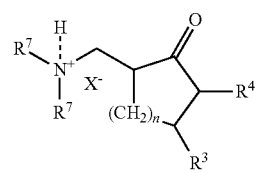
(6)

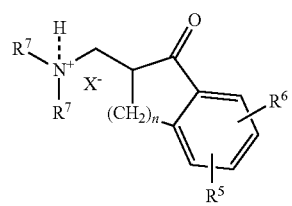
(7)

[$R^1$, $R^2$, $R^3$, $R^4$, $R^5$, $R^6$, and n in the formulae (5) to (7) have the same meanings as those of $R^1$, $R^2$, $R^3$, $R^4$, $R^5$, $R^6$, and n in the formulae (1) to (3), and $R^7$ and $X^-$ in the formulae (5) to (7) have the same meanings as those of $R^7$ and $X^-$ in the formula (4)]; and a second step of reacting the Mannich base and a diene compound with each other by adding an organic solvent, a base in an amount of 1.0 to 20.0 equivalents to the acid, and the diene compound to the reaction liquid, and then heating the reaction liquid, to thereby form a norbornene derivative, the diene compound being represented by the following general formula (8):

[Chem. 5]

(8)

[in the formula (8), $R^8$ represents any one selected from the group consisting of a hydrogen atom, linear chain saturated hydrocarbon groups having 1 to 10 carbon atoms, branched chain saturated hydrocarbon groups having 3 to 10 carbon atoms, and a fluorine atom], the norbornene derivative being represented by any of the following general formulae (9) to (11):

[Chem. 6]

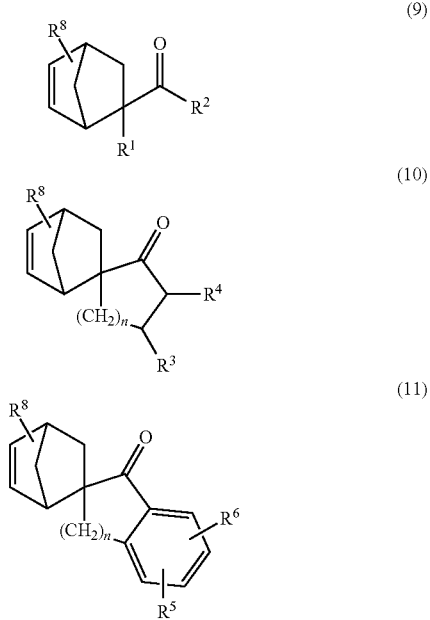

[$R^1$, $R^2$, $R^3$, $R^4$, $R^5$, $R^6$, and n in the formulae (9) to (11) have the same meanings as those of $R^1$, $R^2$, $R^3$, $R^4$, $R^5$, $R^6$, and n in the formulae (1) to (3), and $R^8$ in the formulae (9) to (11) has the same meaning as that of $R^8$ in the formula (8)].

In the method for producing a norbornene derivative of the present invention, the acidic solvent preferably comprises 0.01 to 2.0 mol/L of the acid.

In addition, in the method for producing a norbornene derivative of the present invention, the base added to the reaction liquid is preferably at least one selected from the group consisting of amines, alkali metal hydroxides, and alkaline earth metal hydroxides.

Furthermore, in the method for producing a norbornene derivative of the present invention, the amount of the base added to the reaction liquid is preferably 1.5 to 10.0 equivalents to the acid.

Moreover, in the method for producing a norbornene derivative of the present invention, a heating temperature in the second step is preferably 60 to 180° C.

In addition, in the method for producing a norbornene derivative of the present invention, it is preferable in the second step that a content of the base be 2.0 to 5.0 equivalents to the acid comprised in the reaction liquid, a heating temperature be 85 to 125° C., and a heating time be 0.5 to 1.5 hours.

Moreover, in the method for producing a norbornene derivative of the present invention, the organic solvent added to the reaction liquid is preferably an organic solvent immiscible with a saturated hydrocarbon having 3 to 30 carbon atoms. This makes it possible to liquid-liquid extract the norbornene derivative directly from the reaction liquid with the saturated hydrocarbon having 3 to 30 carbon atoms, and thus to simplify the step. Accordingly, in the method for producing a norbornene derivative of the present invention, it is preferable that the organic solvent added to the reaction liquid be an organic solvent immiscible with a saturated hydrocarbon having 3 to 30 carbon atoms, and that, after the reaction, the norbornene derivative be liquid-liquid extracted directly from the reaction liquid with the saturated hydrocarbon having 3 to 30 carbon atoms.

In addition, in the method for producing a norbornene derivative of the present invention, an organic solvent miscible with a saturated hydrocarbon having 3 to 30 carbon atoms may be used. When the organic solvent added to the reaction liquid is an organic solvent miscible with a saturated hydrocarbon having 3 to 30 carbon atoms as described above, it is preferable to comprise a step in which after the norbornene derivative is formed in the second step, the organic solvent miscible with a saturated hydrocarbon having 3 to 30 carbon atoms is removed from the mixture liquid comprising the norbornene derivative, and then while the mixture liquid from which the organic solvent is removed is used as it is or with water added to the mixture liquid, the norbornene derivative is separated by extraction with the saturated hydrocarbon having 3 to 30 carbon atoms. Specifically, in the step of separation by extraction, it is preferable that a mixture be obtained by removing the organic solvent from the mixture liquid, and while the mixture is used as it is or with water added to the mixture as appropriate, the norbornene derivative be separated by extraction with the saturated hydrocarbon having 3 to 30 carbon atoms. In addition, it is preferable to further comprise, after the step of separation by extraction, a step of washing, with an aqueous alkaline solution and an aqueous acid solution, an extraction liquid comprising the norbornene derivative and the saturated hydrocarbon having 3 to 30 carbon atoms, the norbornene derivative being obtained by separating the norbornene derivative by extraction with the saturated hydrocarbon.

Advantageous Effects of Invention

According to the present invention, it is possible to provide a method for producing a norbornene derivative, which makes it possible to produce a norbornene derivative having a predetermined structure such as a spiro-type norbornene derivative in a sufficiently high yield.

DESCRIPTION OF EMBODIMENTS

Figure 1:
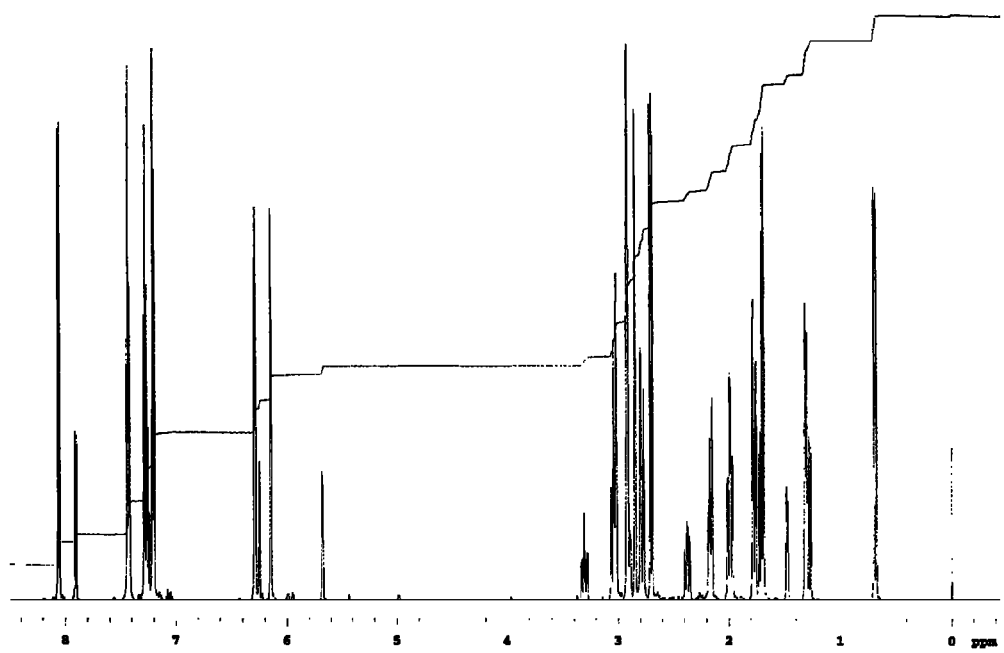
FIG. 1 is a graph of a $^1$H-NMR spectrum (CDCl$_3$) of a compound (TSPNB) obtained in Example 1.

Hereinafter, the present invention will be described in detail on the basis of preferred embodiments thereof.
A method for producing a norbornene derivative of the present invention is a method comprising:

a first step of forming a Mannich base by reacting a carbonyl compound and an amine compound with each other in an acidic solvent, to thereby obtain a reaction liquid comprising the Mannich base in the acidic solvent, the acidic solvent comprising a formaldehyde derivative and 0.01 mol/L or more of an acid represented by a formula: HX (in the formula, X represents any selected from the group consisting of F, Cl, Br, I, $CH_3COO$, $CF_3COO$, $CH_3SO_3$, $CF_3SO_3$, $C_6H_5SO_3$, $CH_3C_6H_4SO_3$, $HOSO_3$, and $H_2PO_4$), the carbonyl compound being represented by any of the above-described general formulae (1) to (3), the amine compound being represented by the above-described general formula (4), the Mannich base being represented by any of the above-described general formulae (5) to (7); and a second step of reacting the Mannich base and a diene compound represented by the above-described general formula (8) with each other by adding an organic solvent, a base in an amount of 1.0 to 20.0 equivalents to the acid, and the diene compound to the reaction liquid, and then heating the reaction liquid, to thereby form a norbornene derivative represented by any of the above-described general formulae (9) to (11). Hereinafter, the first step and the second step of the method for producing a norbornene derivative of the present invention are described separately.

(First Step)

The first step is a step of forming the Mannich base represented by any of the general formulae (5) to (7) by reacting the carbonyl compound represented by any of the general formulae (1) to (3) and the amine compound represented by the general formula (4) in the acidic solvent, to thereby obtain a reaction liquid comprising the Mannich base in the acidic solvent.

The acidic solvent used in the first step comprises a formaldehyde derivative. The formaldehyde derivative is not particularly limited, as long as the formaldehyde derivative can be used for producing a so-called Mannich base. Examples of the formaldehyde derivative include formalin, paraformaldehyde, trioxane, 1,3-dioxolane, 1,3-dioxole, 1,3-dioxane, 1,3-dioxin, 1,3-dioxepane, dihydro-1,3-dioxepin, 1,3-dioxepin, 1,3-dioxocane, dihydro-1,3-dioxocin, 1,3-dioxocin, formaldehyde dimethyl acetal, formaldehyde diethyl acetal, formaldehyde dipropyl acetal, formaldehyde dibutyl acetal, formaldehyde diphenyl acetal, and the like. Of these formaldehyde derivatives, formalin, paraformaldehyde, trioxane, and 1,3-dioxolane are preferable, and formalin and paraformaldehyde are more preferable from the viewpoint of availability. In addition, one of these formaldehyde derivatives alone or a combination of two or more thereof may be used. One of these formaldehyde derivatives alone is preferably used from the viewpoint of purification.

The content of the formaldehyde derivative in the acidic solvent is preferably 2.0 to 50.0% by mass, and more preferably 4.0 to 25.0% by mass. If the content of the formaldehyde derivative is less than the lower limit, the yield of the Mannich base represented by any of the general formulae (5) to (7) tends to be low. Meanwhile, if the content exceeds the upper limit, the yield tends to be low, and purification tends to be difficult.

In addition to the formaldehyde derivative, the acidic solvent used in the first step comprises the acid represented by the formula: HX (in the formula, X represents any selected from the group consisting of F, Cl, Br, I, $CH_3COO$, $CF_3COO$, $CH_3SO_3$, $CF_3SO_3$, $C_6H_5SO_3$, $CH_3C_6H_4SO_3$, $HOSO_3$, and $H_2PO_4$). The kind of the acid (HX) is not particularly limited, as long as the acid is represented by the formula:

HX. From the viewpoint of the stability of the Mannich base represented by any of the general formulae (5) to (7), an acid whose X in the formula: HX is F, Cl, Br, $CH_3COO$, or $CF_3COO$ is more preferable, and an acid whose X is Cl or $CH_3COO$ is further preferable.

In the acidic solvent, the content of the acid (HX) needs to be 0.01 mol/L or more (more preferably 0.02 to 2.0 mol/L, and further preferably 0.04 to 1.0 mol/L). If the content of the acid is less than the lower limit, the yield of the Mannich base prepared in the first step and represented by any of the general formulae (5) to (7) is insufficient, and it is impossible to prepare the norbornene derivative efficiently. Meanwhile, if the content of the acid (HX) exceeds the upper limit, the yield tends to be low and purification tends to be difficult.

Moreover, the acidic solvent may comprises another solvent, in addition to the formaldehyde derivative and the acid. Examples of the solvent include water, alcohols, glycols, glycerin, ethers, cellosolves, nitriles, amides, and the like. In addition, the content of the solvent in the acidic solvent is preferably 20 to 60% by mass, and more preferably 30 to 50% by mass. If the content of the solvent is less than the lower limit, the mixing tends to be non-uniform, so that the yield of the Mannich base represented by any of the general formulae (5) to (7) tends to be insufficient. Meanwhile, if the content of the solvent exceeds the upper limit, the reaction rate tends to be lowered, so that the yield tends to decrease.

In addition, in the first step, the use of the acidic solvent comprising the formaldehyde derivative and 0.01 mol/L or more of the acid (the acid represented by the formula: HX) enables the carbonyl compound and the amine compound to react with each other under an acidic condition where the acid is present in excess. This makes it possible to efficiently produce the Mannich base represented by any of the general formulae (5) to (7), which is a reaction intermediate used for the preparation of the norbornene derivative.

In addition, the carbonyl compound used in the first step is a carbonyl compound represented by any of the following general formulae (1) to (3):

[Chem. 7]

(1)

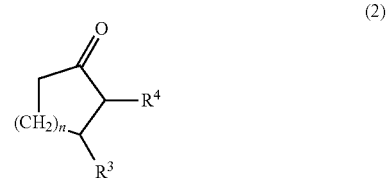

(2)

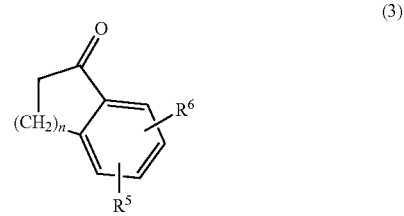

(3)

[in the formulae (1) to (3), $R^1$, $R^2$, $R^3$, $R^4$, $R^5$, and $R^6$ each independently represent any one selected from the group consisting of a hydrogen atom, linear chain saturated hydrocarbon groups having 1 to 10 carbon atoms, branched chain saturated hydrocarbon groups having 3 to 10 carbon atoms, saturated cyclic hydrocarbon groups having 3 to 8 carbon atoms, aryl groups having 6 to 12 carbon atoms, aralkyl groups having 7 to 13 carbon atoms, alkoxy groups having 1 to 10 carbon atoms, a fluorine atom, a chlorine atom, and a bromine atom, and n represents an integer of any of 0 to 4].

The linear chain saturated hydrocarbon group which can be selected as $R^1$, $R^2$, $R^3$, $R^4$, $R^5$, or $R^6$ in the general formulae (1) to (3) is one having 1 to 10 carbon atoms. As the linear chain saturated hydrocarbon group, one having 1 to 6 carbon atoms is more preferable, and one having 1 to 4 carbon atoms is further preferable. If the number of carbon atoms exceeds the upper limit, purification tends to be difficult. In addition, as the linear chain saturated hydrocarbon group, a methyl group or an ethyl group is more preferable, from the viewpoint of ease of purification.

Meanwhile, the branched chain saturated hydrocarbon group which can be selected as $R^1$, $R^2$, $R^3$, $R^4$, $R^5$, or $R^6$ is one having 3 to 10 carbon atoms. As the branched chain saturated hydrocarbon group, one having 3 to 6 carbon atoms is more preferable, and one having 3 to 5 carbon atoms is further preferable. If the number of carbon atoms of the branched chain saturated hydrocarbon group exceeds the upper limit, purification tends to be difficult. In addition, as the branched chain saturated hydrocarbon group, an isopropyl is more preferable from the viewpoint of ease of purification.

Moreover, the saturated cyclic hydrocarbon group which can be selected as $R^1$, $R^2$, $R^3$, $R^4$, $R^5$, or $R^6$ is one having 3 to 8 carbon atoms. As the saturated cyclic hydrocarbon group, one having 4 to 7 carbon atoms is more preferable, and one having 5 to 6 carbon atoms is further preferable. If the number of carbon atoms of the saturated cyclic hydrocarbon group exceeds the upper limit, purification becomes difficult. Meanwhile, if the number of carbon atoms is less than the lower limit, the chemical stability tends to be poor. In addition, as the saturated cyclic hydrocarbon group, a cyclopentyl or a cyclohexyl is more preferable, from the viewpoints of ease of purification and chemical stability.

In addition, the aryl group which can be selected as $R^1$, $R^2$, $R^3$, $R^4$, $R^5$, or $R^6$ is one having 6 to 12 carbon atoms. As the aryl group, one having 6 to 10 carbon atoms is more preferable. If the number of carbon atoms of the aryl group exceeds the upper limit, purification tends to be difficult. In addition, as the aryl group, a phenyl group or a naphthyl group is more preferable, from the viewpoint of ease of purification.

Moreover, the aralkyl group which can be selected as $R^1$, $R^2$, $R^3$, $R^4$, $R^5$, or $R^6$ is one having 7 to 13 carbon atoms. As the aralkyl groups, one having 7 to 11 carbon atoms is more preferable. If the number of carbon atoms of the aralkyl group exceeds the upper limit, purification tends to be difficult. In addition, as the aralkyl groups, a benzyl group, a phenylethyl group, or a naphthylmethyl group is more preferable, from the viewpoint of ease of purification.

Furthermore, the alkoxy group which can be selected as $R^1$, $R^2$, $R^3$, $R^4$, $R^5$, or $R^6$ is one having 1 to 10 carbon atoms. As the alkoxy group, one having 1 to 5 carbon atoms is more preferable, and one having 1 to 3 carbon atoms is further preferable. If the number of carbon atoms of the alkoxy group exceeds the upper limit, purification tends to be difficult. In addition, as the alkoxy group, a methoxy group or an ethoxy group is more preferable, from the viewpoint of ease of purification.

In addition, as the substituent which can be selected as $R^1$, $R^2$, $R^3$, $R^4$, $R^5$, or $R^6$, a hydrogen atom or a methyl group is more preferable among the above-described substituents, from the viewpoint of ease of purification.

Moreover, n in the general formulae (2) and (3) is an integer of any of 0 to 4. If the value of n exceeds the upper limit, purification tends to be difficult. In addition, the value of n is more preferably an integer of any of 1 and 2, from the viewpoint of ease of purification.

Examples of the carbonyl compound represented by any of the general formulae (1) to (3) include acetone, butanone, pentanone, hexanone, heptanone, octanone, nonanone, decanone, undecanone, dodecanone, tridecanone, tetradecanone, pentadecanone, hexadecanone, heptadecanone, octadecanone, nonadecanone, eicosanone, none methyl ethyl ketone, acetophenone, propiophenone, propyl phenyl ketone, butyl phenyl ketone, pentyl phenyl ketone, hexyl phenyl ketone, heptyl phenyl ketone, octyl phenyl ketone, nonyl phenyl ketone, decyl phenyl ketone, tolperisone, eperison, 4-hydroxyacetophenone, acetylthiophene, methyl isopropyl ketone, cyclopropanone, cyclobutanone, cyclopentanone, cyclohexanone, cycloheptanone, cyclooctanone, cyclononanone, cyclodecanone, benzocyclobutanone, indanone, tetralone, benzosuberone, methyronaphthone, ethyronaphthone, propionaphthone, butyronaphthone, pentyronaphthone, hexyronaphthone, heptyronaphthone, octyronaphthone, nonyronaphthone, decyronaphthone, naphthalenone, deoxybenzoin, cyclopentyl methyl ketone, cyclopentyl ethyl ketone, cyclopentyl propyl ketone, cyclopentyl butyl ketone, cyclopentyl pentyl ketone, cyclopentyl hexyl ketone, cyclopentyl heptyl ketone, cyclopentyl octyl ketone, cyclopentylnonyl ketone, cyclopentyl decyl ketone, cyclohexyl methyl ketone, cyclohexyl ethyl ketone, cyclohexyl propyl ketone, cyclohexyl butyl ketone, cyclohexyl pentyl ketone, cyclohexyl hexyl ketone, cyclohexyl heptyl ketone, cyclohexyl octyl ketone, cyclohexyl nonyl ketone, cyclohexyl decyl ketone, cyclopentylacetone, cyclohexylacetone, camphor, fluoroacetophenone, chloroacetophenone, bromoacetophenone, methoxyacetophenone, ethoxyacetophenone, propoxyacetophenone, butoxyacetophenone, methylacetophenone, ethylacetophenone, propylacetophenone, butylacetophenone, pentylacetophenone, hexylacetophenone, heptylacetophenone, octylacetophenone, 1'-acetonaphthone, 1,3-diphenyl-2- propanone, 1-acetyladamantane, 1- bromo-3,3- dimethyl-2-butanone, 1-phenyl-2-butanone, 10-nonadecanone, 11- heneicosanone, 12-tricosanone, 14-heptacosanone, 16-hentriacontanone, 18-pentatriacontanone, 2',4'-dichlorobutyrophenone, 2',4'-dihydroxypropiophenone, 2'-acetonaphthone, 2-ethylpropiophenone, 2'-fluoropropiophenone, 2'-hydroxyacetophenone, 2'-hydroxypropiophenone, 2,5-dimethyl-3-hexanone, 2,6-dimethyl-4-heptanone, 2-acetylfuran, 2-acetylthiophene, 2-bromoacetylnaphthalene, 2-butanone, 2-decanone, 2-dodecanone, 2-heptanone, 2-hexanone, 2-methyl-1,2'-dinaphthyl ketone, 2-methyl-3-heptanone, 2-methyl-3-hexanone, 2-methyl-3-pentanone, 2-methyl-4-heptanone, 2-methyl-4-undecanone, 2-nonanone, 2-octanone, 2-pentadecanone, 2-pentanone, 2-propionylthiophene, 2-tetradecanone, 2-tridecanone, 2-undecanone, 3',4'-dichloropropiophenone, 3'-chloropropiophenone, 3'-hydroxyacetophenone, 3'-nitropropiophenone, 3-acetylthiophene, 3-bromo-3-methyl-2-butanone, 3-chloro-2-butanone, 3-decanone, 3-dodecanone, 3-heptanone, 3-hexadecanone, 3-hexanone, 3-hexyn-2-one, 3-methyl-2-butanone, 3-methyl-2-hexanone, 3-methyl-2-pentanone, 3-methyl-3-buten-2-one, 3-methyl-4-heptanone, 3-nonanone, 3-octanone, 3-pentanone, 3-tetradecanone, 3-undecanone, 4'-chlorobutyrophenone, 4'-chloropropiophenone, 4'-ethylpropiophenone, 4'-fluoropropiophenone, 4'-hydroxyacetophenone, 4'-hydroxybutyrophenone, 4'-hydroxyheptanophenone, 4'-hydroxyhexanophenone, 4'-hydroxypropiophenone, 4-decanone, 4-dibenzyl-1-naphthyl ketone, 4-heptanone, 4-hydroxy-2-butanone, 4-methyl-2-pentanone, 4-methylbenzyl phenyl ketone, 4-nonanone, 4-octanone, 4-undecanone, 5-acetyl-2-norbornene, 5-chloro-2-pentanone, 5-dodecanone, 5-hexen-2-one, 5-methyl-2-octanone, 5-methyl-3-heptanone, 5-nonanone, 5-undecanone, 6-acetyl-1,4-benzodioxane, 6-chloro-2-hexanone, 6-methyl-2-heptanone, 6-undecanone, 7-tridecanone, 8-pentadecanone, 9-heptadecanone, acetophenone, acetylcyclobutane, benzalacetone, benzyl 4-bromophenyl ketone, benzyl 4-fluorophenyl ketone, benzyl butyl ketone, benzyl isopropyl ketone, benzyl phenyl ketone, benzylacetone, butyrophenone, cyclopentanone, cyclopropyl-2-thienyl ketone, cyclopropyl methyl ketone, decanophenone, dodecanophenone, ethyl isobutyl ketone, ethyl perfluoroamyl ketone, heptanophenone, hexanophenone, isoamyl methyl ketone, isobutyl styryl ketone, isovalerophenone, methyl pentadecafluoroheptyl ketone, methyl perfluoroamyl ketone, methyl perfluoro-n-butyl ketone, methyl vinyl ketone, n-hexadecanophenone, n-nonadecanophenone, n-nonanophenone, n-octanophenone, n-undecanophenone, octadecanophenone, phenyl 1-propenyl ketone, pinacolin, piperonyl methyl ketone, propiophenone, tetradecanophenone, trans,trans-1,5-bis(4-fluorophenyl)-1,4-pentadien-3-on e, trans,trans-1,5-diphenyl-1,4-pentadien-3-one, tridecanophenone, valerophenone, and the like.

In addition, the method for preparing the carbonyl compound represented by any of the general formulae (1) to (3) is not particularly limited, and a known method can be employed as appropriate. Moreover, as the compound represented by any of the general formulae (1) to (3), commercially available product may be used.

Meanwhile, the amine compound used in the first step is an amine compound represented by the following general formula (4):

[Chem. 8]

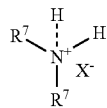

(4)

[in the formula (4), $R^7$s each independently represent any one selected from the group consisting of linear chain saturated hydrocarbon groups having 1 to 20 carbon atoms, branched chain saturated hydrocarbon groups having 3 to 20 carbon atoms, saturated cyclic hydrocarbon groups having 3 to 20 carbon atoms, and saturated hydrocarbon groups having a hydroxyl group and 1 to 10 carbon atoms, the two $R^7$s may be bonded to each other to form anyone ring selected from the group consisting of a pyrrolidine ring, a piperidine ring, a piperazine ring, and a morpholine ring, and $X^-$ represents anyone selected from the group consisting of $F^-$, $Cl^-$, $Br^-$, $I^-$, $CH_3COO^-$, $CF_3COO^-$, $CH_3SO_3^-$, $CF_3SO_3^-$, $C_6H_5SO_3^-$, $CH_3C_6H_4SO_3^-$, $HOSO_3^-$, and $H_2PO_4^-$].

The linear chain saturated hydrocarbon group which can be selected as $R^7$ in the general formula (4) is one having 1 to 20 carbon atoms. The linear chain saturated hydrocarbon group has more preferably 1 to 10 carbon atoms, and further preferably 1 to 5 carbon atoms. If the number of carbon atoms of the linear chain saturated hydrocarbon group exceeds the upper limit, purification tends to be difficult. As the linear chain saturated hydrocarbon group which can be selected as $R^7$, a methyl group or an ethyl group is more preferable, from the viewpoint of ease of purification.

Meanwhile, the branched chain saturated hydrocarbon group which can be selected as $R^7$ is one having 3 to 20 carbon atoms. The branched chain saturated hydrocarbon group has more preferably 3 to 10 carbon atoms, and further preferably 3 to 5 carbon atoms. If the number of carbon atoms of the branched chain saturated hydrocarbon group exceeds the upper limit, purification tends to be difficult. As the branched chain saturated hydrocarbon group which can be selected as $R^7$, an isopropyl group is more preferable from the viewpoint of ease of purification.

Moreover, the saturated cyclic hydrocarbon group which can be selected as $R^7$ is one having 3 to 20 carbon atoms. The saturated cyclic hydrocarbon group has more preferably 3 to 10 carbon atoms, and further preferably 5 to 6 carbon atoms. If the number of carbon atoms of the saturated cyclic hydrocarbon group exceeds the upper limit, purification becomes difficult. Meanwhile, if the number of carbon atoms is less than the lower limit, chemical stability tends to be poor. As the saturated cyclic hydrocarbon group which can be selected as $R^7$, a cyclopentyl group or a cyclohexyl group is more preferable, from the viewpoints of ease of purification and chemical stability.

The saturated hydrocarbon group having a hydroxyl group which can be selected as $R^7$ is one whose hydrocarbon group has 1 to 10 carbon atoms. In the saturated hydrocarbon group having a hydroxyl group, the number of carbon atoms is more preferably 2 to 10, and further preferably 2 to 5. If the number of carbon atoms of the saturated hydrocarbon group having a hydroxyl group exceeds the upper limit, purification becomes difficult. Meanwhile, if the number of carbon atoms is less than the lower limit, chemical stability tends to be poor. As the saturated hydrocarbon group having a hydroxyl group which can be selected as $R^7$, a 2-hydroxyethyl group is more preferable, from the viewpoints of ease of purification and chemical stability.

In addition, the two $R^7$s in the general formula (4) may be bonded to each other to form any one of a pyrrolidine ring, a piperidine ring, a piperazine ring, and a morpholine ring. Specifically, regarding the two $R^7$s in the general formula (4), the $R^7$s may be bonded to each other to form a pyrrolidine ring, a piperidine ring, a piperazine ring, or a morpholine ring, together with the nitrogen atom (N) in the formula (4). When the $R^7$s are bonded to each other to form a ring as described above, morpholine is more preferable from the viewpoint of odor.

Moreover, as $R^7$s in the general formula (4), methyl groups, ethyl groups, 2-hydroxyethyl groups, or morpholine is more preferable, from the viewpoint of ease of purification.

$X^-$ in the general formula (4) is a so-called counter anion. $X^-$ is any one selected from the group consisting of $F^-$, $Cl^-$, $Br^-$, $I^-$, $CH_3COO^-$, $CF_3COO^-$, $CH_3SO_3^-$, $CF_3SO_3^-$, $C_6H_5SO_3^-$, $CH_3C_6H_4SO_3^-$, $HOSO_3^-$, and $H_2PO_4^-$. As $X^-$, $CH_3COO^-$, or $CF_3COO^-$ is preferable, and $Cl^-$ or $CH_3COO^-$ is more preferable, from the viewpoint of the stability of the Mannich base represented by any of the general formulae (5) to (7).

In addition, examples of the amine compound represented by the general formula (4) include salts (secondary amine salts in which the aforementioned $X^-$ serves as an counter anion) of secondary amines such as dimethylamine, diethylamine, di-n-propylamine, diisopropylamine, di-n-butylamine, diisobutylamine, di-sec-butylamine, di-t-butylamine, dipentylamine, dicyclopentylamine, dihexylamine, dicyclohexylamine, diheptylamine, dioctylamine, di(2-ethylhexyl)amine, dinonylamine, didecylamine, diundecylamine, didodecylamine, ditridecylamine, ditetradecylamine, dipentadecylamine, dihexadecylamine, diheptadecylamine, dioctadecylamine, dinonadecylamine, morpholine, diethanolamine, aziridine, azetidine, pyrrolidine, piperidine, indoline, and isoindoline.

Moreover, in the first step, the carbonyl compound represented by any of the general formulae (1) to (3) and the amine compound represented by the general formula (4) are reacted with each other in the acidic solution. The reaction conditions for reacting the carbonyl compound and the amine compound in the acidic solution are not particularly limited, and can be changed as appropriate depending on the kind of the solvent used, and the like.

As for the reaction conditions, an atmosphere with which the acidic solution is in contact is preferably an atmosphere of inert gas such as nitrogen gas. In addition, from the viewpoint of promoting the reaction, the reaction is preferably caused to proceed under heated conditions. As the heated conditions, conditions that the heating is conducted at a temperature of 60 to 140° C. (more preferably 80 to 120° C.) for 0.5 to 10 hours (more preferably 1 to 5 hours) are preferably employed. If the heating temperature and/or the heating time are less than the lower limits, the yield of the Mannich base represented by any of the general formulae (5) to (7) tends to be low. Meanwhile, if the heating temperature and time exceed the upper limits, by-products such as vinyl ketone and vinyl ketone dimer tend to increase, so that the yield of the Mannich base represented by any of the general formulae (5) to (7) tends to be low.

By reacting the carbonyl compound represented by any of the general formulae (1) to (3) and the amine compound represented by the general formula (4) with each other in the presence of the acidic solvent as described above, it is possible to form the Mannich base represented by any of the following general formulae (5) to (7):

[Chem. 9]

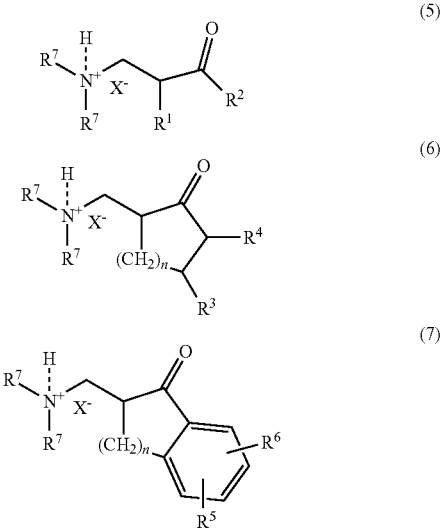

[$R^1$, $R^2$, $R^3$, $R^4$, $R^5$, $R^6$, and n in the formulae (5) to (7) have the same meanings as those of $R^1$, $R^2$, $R^3$, $R^4$, $R^5$, $R^6$, and n in the formulae (1) to (3), and $R^7$ and $X^-$ in the formulae (5) to (7) have the same meanings as those of $R^7$ and $X^-$ in the formula (4)]. Thus, the reaction liquid comprising the Mannich base in the acidic solvent can be obtained. Note that, in the first step, by use of the acidic solvent, the carbonyl compound and the amine compound are reacted with each other under an acidic condition where the acid (HX) is present in excess (under an acidic condition where 0.01 mol/L or more of the acid (HX) is present). This makes it possible to form the Mannich base represented by any of the general formulae (5) to (7) in a sufficiently high yield. In the present invention, the production efficiency and the yield of the reaction intermediate (the Mannich base) are sufficiently improved in the first step as described above. Then, in the present invention, the reaction liquid comprising the thus formed Mannich base represented by any of the general formulae (5) to (7) is directly used in the second step. Hence, the Mannich base can be used efficiently. It is presumed that this aspect also leads to the improvement in the yield of the final target product.

(Second Step)

The second step is a step of reacting the Mannich base and a diene compound represented by the general formula (8) with each other by adding an organic solvent, a base in an amount of 1.0 to 20.0 equivalents to the acid, and the diene compound to the reaction liquid, and then heating the reaction liquid, to thereby form a norbornene derivative represented by any of the general formulae (9) to (11).

In the second step, the reaction liquid obtained in the first step is used. In the present invention, the Mannich base represented by any of the general formulae (5) to (7) is thus not isolated from the reaction liquid in the second step. Hence, Mannich base, which is the reaction intermediate, in the reaction liquid can be used highly efficiently, and the step can be simplified. These enable sufficiently efficient production of the norbornene derivative.

Moreover, in the second step, the organic solvent is added to the reaction liquid. The organic solvent is not particularly limited, and organic solvents which can be used for the so-called Diels-Alder reaction can be used as appropriate. In addition, the organic solvent is not particularly limited, and examples thereof include alcohol-based solvents (including glycol-based solvents, glycerin-based solvents, and other polyvalent alcohol-based solvents), cellosolve-based solvents, ether-based solvents, amide-based solvents, and nitrile-based solvents. A proffered organic solvent can be selected and used as appropriate depending on the kind of the target norbornene derivative, and the like.

In addition, the organic solvent is preferably an organic solvent immiscible with a saturated hydrocarbon having 3 to 30 carbon atoms, from the viewpoint of simplifying an extraction step which follows the reaction. As the organic solvent immiscible with a saturated hydrocarbon having 3 to 30 carbon atoms, methanol, methyl cellosolve, dimethylacetamide, dimethyl sulfoxide, ethylene glycol, propylene glycol, 1,3-propanediol, glycerin, propylene glycol monomethyl ether, ethyl cellosolve, dimethylformamide, acetonitrile, or the like is preferable. From the viewpoints of ease and convenience of extraction operations, methanol or methyl cellosolve is more preferable.

In addition, the added amount of the organic solvent added to the reaction liquid is not particularly limited, and is preferably 10 to 80% by mass (more preferably 20 to 60% by mass) relative to the total amount of the reaction liquid and the organic solvent added. If the amount of the organic solvent added is less than the lower limit, the reaction rate tends to be low, and hence the yield tends to decrease. Meanwhile, if the amount of the organic solvent added exceeds the upper limit, by-products such as vinyl ketone dimer tend to increase, so that the yield of the target product tends to be low.

In addition, the base is added to the reaction liquid in the second step. The kind of the base added to the reaction liquid is not particularly limited, and amines, alkali metal hydroxides, and alkaline earth metal hydroxides can be used preferably, from the viewpoint of basicity. Of these bases, dimethylamine, diethylamine, dipropylamine, and dibutylamine are preferable, and dimethylamine is particularly preferable, from the viewpoint of purification.

In addition, the added amount of the base added to the reaction liquid needs to be an amount of 1.0 to 20.0 equivalents to (more preferably 1.5 to 10.0 equivalents to, and further preferably 2.0 to 5.0 equivalents to) the acid comprised in the reaction liquid. If the amount of the base added is less than the lower limit, the degradation of the Mannich base represented by any of the general formulae (5) to (7) is suppressed, so that the target vinyl ketone intermediate, which is the raw material, is not produced. Meanwhile, if the amount of the base added exceeds the upper limit, the extraction becomes difficult because a large amount of a neutralizing agent is necessary during the purification. As described above, in the present invention, by making the reaction liquid neutral or basic, the Mannich base represented by any of the general formulae (5) to (7) and the diene compound of the general formula (8) are reacted with each other in the second step. Thus, the formation of by-products (for example, a dimerization product (dimer) formed due to dimerization by the hetero Diels-Alder reaction of a vinyl ketone formed by elimination of an amine compound from the Mannich base) is sufficiently suppressed, so that the target norbornene derivative can be produced in a sufficiently high selectivity.

Moreover, in the second step, the diene compound is added to the reaction liquid. The diene compound is represented by the following general formula (8):

[Chem. 10]

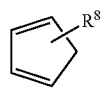

(8)

[in the formula (8), R$^8$ represents any one selected from the group consisting of a hydrogen atom, linear chain saturated hydrocarbon groups having 1 to 10 carbon atoms, branched chain saturated hydrocarbon groups having 3 to 10 carbon atoms, and a fluorine atom].

The linear chain saturated hydrocarbon group which can be selected as R$^8$ in the general formula (8) is one having 1 to 10 carbon atoms. In the linear chain saturated hydrocarbon group, the number of carbon atoms is more preferably 1 to 5, and further preferably 1 to 3. If the number of carbon atoms of the linear chain saturated hydrocarbon group exceeds the upper limit, purification tends to be difficult. As the linear chain saturated hydrocarbon group, a methyl group, an ethyl group, or a propyl group is more preferable, from the viewpoint of purification.

In addition, the branched chain saturated hydrocarbon group which can be selected as R$^8$ is one having 3 to 10 carbon atoms. In the branched chain saturated hydrocarbon group, the number of carbon atoms is more preferably 3 to 7 carbon atoms, and further preferably 3 to 5. If the number of carbon atoms of the branched chain saturated hydrocarbon group exceeds the upper limit, purification tends to be difficult. In addition, as the branched chain saturated hydrocarbon group, an isopropyl group is more preferable from the viewpoint of purification.

In addition, as R$^8$, hydrogen or a methyl group is more preferable from the viewpoints of availability and purification.

In addition, in the second step, after the organic solvent, the base, and the diene compound represented by the general formula (8) are added to the reaction liquid, the Mannich base and the diene compound are reacted with each other by heating the obtained mixture liquid.

Any conditions can be employed for the heating, as long as the norbornene derivative can be produced by reacting the Mannich base represented by any of the general formulae (5) to (7) and the diene compound represented by the general formula (8) with each other in the mixture liquid. A heating temperature for reacting the Mannich base and the diene compound with each other is preferably 60 to 180° C. (more preferably 80 to 140° C.). If the heating temperature is lower than the lower limit, the degradation rate of the Mannich base tends to low, so that the yield of the target product tends to decrease. Meanwhile, if the heating temperature exceeds the upper limit, by-products such as vinyl ketone dimer and tetracyclododecene which is formed by a Diels-Alder addition of another molecule of the diene to the target product tend to increase, so that the selectivity for the target product tends to be low.

In addition, a heating time for reacting the Mannich base and the diene compound with each other is preferably 0.01 to 5.0 hours, and more preferably 0.1 to 1.5 hours. If the heating time is less than the lower limit, the yield tends to be low. Meanwhile, if the heating time exceeds the upper limit, by-products tend to increase. Note that an atmosphere during the heating is preferably an atmosphere of inert gas such as nitrogen gas, from the viewpoints of coloring prevention and safety.

In addition, as a method for the heating, it is possible to employ a method in which a mixture liquid of the Mannich base represented by any of the general formulae (5) to (7), the diene compound represented by the general formula (8), the base, and the organic solvent is added dropwise to a reaction vessel preheated to the heating temperature. In addition, when the method in which the mixture liquid is added dropwise as described above is employed, a portion of the organic solvent may be placed in the reaction vessel beforehand. This enables the reaction to proceed more safely.

In addition, when an organic solvent having a boiling point lower than the heating temperature is used, a pressure container such as an autoclave may be employed. In this case, the heating may be started at normal pressure, or at a predetermined pressure. This allows various kinds of organic solvents to be used, and also enables reduction in thermal energy for solvent recycling.

By adding the organic solvent, the base, and the diene compound to the reaction liquid, and then heating the mixture liquid, as described above, the norbornene derivative represented by any of the following general formulae (9) to (11) can be obtained:

[Chem. 11]

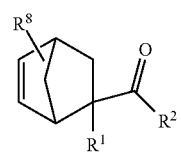

(9)

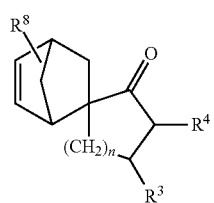

(10)

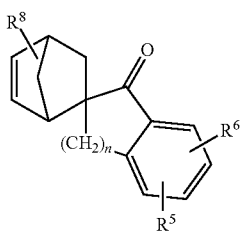

(11)

[$R^1$, $R^2$, $R^3$, $R^4$, $R^5$, $R^6$, and n in the formulae (9) to (11) have the same meanings as $R^1$, $R^2$, $R^3$, $R^4$, $R^5$, $R^6$, and n in the formulae (1) to (3), and $R^8$ in the formulae (9) to (11) has the same meaning as that of $R^8$ in the formula (8)]. In the reaction for obtaining the norbornene derivative, first, by heating the mixture liquid, which is obtained by adding the organic solvent, the base, and the diene compound to the reaction liquid, an amine compound is eliminated from the Mannich base represented by any of the general formulae (5) to (7) under a neutral or basic condition, so that a compound having a vinyl ketone structure represented by any of the following general formula (12) to (14) is formed:

[Chem. 12]

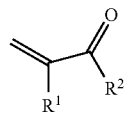

(12)

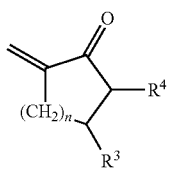

(13)

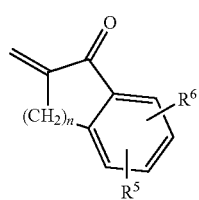

(14)

[$R^1$, $R^2$, $R^3$, $R^4$, $R^5$, $R^6$, and n in the formulae (12) to (14) have the same meanings as those of $R^1$, $R^2$, $R^3$, $R^4$, $R^5$, $R^6$, and n in the formulae (1) to (3)].

Subsequently, the compound having the vinyl ketone structure and the diene compound represented by the general formula (8) are reacted with each other by the so-called Diels-Alder reaction, so that the norbornene derivative represented by any of the general formulae (9) to (11) is formed. Note that, by causing the reaction to proceed under a neutral or basic condition as described above, the formation of by-products can be suppressed at a higher level, and the norbornene derivative can be produced efficiently.

After formation of the norbornene derivative by the reaction, the percentage of the compound having the vinyl ketone structure present in the mixture liquid after the reaction is preferably 2 mol % or less relative to the norbornene derivative (the target product). If the percentage of the compound having the vinyl ketone structure present exceeds the upper limit, the target product tends to be colored, or a product tends to be viscous due to dimerization. Note that, from the viewpoint that the percentage of the compound having the vinyl ketone structure present is more surely made 2 mol % or less, it is preferable to make the content of the base 2.0 to 5.0 equivalents to the acid comprised in the reaction liquid, the heating temperature 85 to 125° C., and the heating time 0.5 to 1.5 hours, in the second step.

In addition, after the formation of the norbornene derivative by the reaction, the percentage of the dimerization product (dimer), which is formed by dimerization of the compound having the vinyl ketone structure, present in the mixture liquid after the reaction is preferably 2 mol % or less relative to the norbornene derivative (the target product). If the percentage of the dimmers present exceeds the upper limit, a product tends to be viscous. Note that, from the viewpoint that the percentage of the dimmer present is more surely made 2 mol % or less, it is preferable to the content of the base 2.0 to 5.0 equivalents to the acid comprised in the reaction liquid, the heating temperature 85 to 125° C., and the heating time 0.5 to 1.5 hours, in the second step. Note that the percentages of the compound having the vinyl ketone structure and the dimmer present in the mixture liquid can be measured by the so-called HPLC analysis. As the apparatus using for the HPLC analysis and the like, known apparatus and the like can be used as appropriate.

In addition, after the formation of the norbornene derivative by the reaction, a method for extracting the norbornene derivative from the mixture liquid after the reaction is not particularly limited, and a known method may be employed as appropriate. In addition, as the extraction method, it is preferable to employ a method in which the solvent is removed from the mixture liquid in which the norbornene derivative is formed, and then while the obtained mixture is used as it is or with water added thereto as appropriate, the norbornene derivative is separated by extraction with a saturated hydrocarbon having 3 to 30 carbon atoms (more preferably 5 to 10 carbon atoms). By extracting the norbornene derivative by using such a saturated hydrocarbon, by-products such as amine salts and heavy products can be removed easily and conveniently. In addition, when water is added to the mixture in the step, the amount of water added is not particularly limited, and may be changed as appropriate depending on the amount of the mixture to be obtained, the apparatus used for the extraction, and the like. Moreover, in the present invention, from the viewpoint of separating the norbornene derivative by extraction more efficiently, it is preferable to employ a method in which the norbornene derivative is formed by using an organic solvent immiscible with a saturated hydrocarbon having 3 to 30 carbon atoms as the organic solvent added to the reaction liquid, and after that the norbornene derivative is separated by liquid-liquid extraction by using the saturated hydrocarbon having 3 to 30 (more preferably 5 to 10) carbon atoms in the mixture liquid after the reaction. Note that the method for isolating and purifying the norbornene derivative after the extraction liquid is obtained by separating the norbornene derivative by extraction as described above is not particularly limited, and a known method can be employed as appropriate.

In addition, in the present invention, it is preferable to further comprise, after the step of separation by extraction, a step of washing, with an aqueous alkaline solution and an aqueous acid solution, an extraction liquid comprising the norbornene derivative and the saturated hydrocarbon having 3 to 30 carbon atoms, the norbornene derivative being obtained by separating the norbornene derivative by extraction with the saturated hydrocarbon. In addition, in the washing treatment, it is desirable to wash the extraction liquid with an aqueous alkaline solution comprising an amine, an alkali metal hydroxide, an alkaline earth metal hydroxide, or the like, and subsequently with an aqueous acid solution comprising an inorganic acid, an organic acid, or the like, thereafter to neutralize the extraction liquid with weakly alkaline or weakly acidic water, and to dehydrate the extraction liquid with an dehydrating agent such as saturated aqueous sodium chloride. As the aqueous alkaline solution, aqueous ammonia, aqueous sodium hydroxide, aqueous potassium hydroxide, aqueous calcium hydroxide, or the like is preferable, and aqueous sodium hydroxide is particularly preferable. In addition, the concentration of the alkali component in the aqueous alkaline solution is preferably about 1 to 20% by mass. By washing the extraction liquid comprising the norbornene derivative with such an aqueous alkaline solution, by-products such as amine salts and heavy products can be removed easily and conveniently. Meanwhile, as the aqueous acid solution, aqueous hydrochloric acid, aqueous sulfuric acid, aqueous phosphoric acid, aqueous nitric acid, aqueous acetic acid, or the like is preferable, and aqueous hydrochloric acid is particularly preferable. In addition, the concentration of the acid in the aqueous acid solution is preferably about 1 to 20% by mass. By washing the extraction liquid comprising the norbornene derivative with such an aqueous acid solution, by-products such as amine salts and heavy products can be removed easily and conveniently. In addition, regarding the sequence of the washings, the washing with the aqueous acid solution may be conducted before the washing with the aqueous alkaline solution. In addition, as the weakly alkaline water used for the neutralization in the washing treatment, aqueous sodium carbonate, aqueous sodium hydrogen carbonate, aqueous potassium carbonate, aqueous sodium acetate, or the like is preferable, and aqueous sodium hydrogen carbonate is particularly preferable. The use of the weakly alkaline water enables the pH of the liquid to be made around neutral in a short period of time, and also enables degradation to be suppressed during the subsequent distillation purification. In addition, as the weakly acidic water used for the neutralization in the washing treatment, aqueous ammonium chloride, aqueous ammonium sulfate, aqueous ammonium nitrate, aqueous ammonium phosphate, or the like is preferable, and aqueous ammonium chloride is particularly preferable. The use of the weakly acidic water enables the pH of the liquid to be made around neutral in a short period of time, and also enables degradation to be suppressed during the subsequent distillation purification. Moreover, as the dehydrating agent used in the washing treatment, saturated aqueous sodium chloride, anhydrous magnesium sulfate, anhydrous sodium sulfate, silica gel, calcium oxide, diphosphorus pentoxide, or the like is preferable, and saturated aqueous sodium chloride or anhydrous magnesium sulfate is particularly preferable. Moreover, azeotropic dehydration with addition of benzene, toluene, or the like can also be employed. By dehydrating the extraction liquid comprising the norbornene derivative by using the dehydrating agent, the water in the liquid can be reduced, and separation of water can be suppressed during subsequent concentrating of the extraction liquid.

According to the method for producing a norbornene derivative, the norbornene derivative having a spiro-type structure or the like and being represented by any of the general formulae (9) to (11) can be produced in a sufficient yield. In addition, according to the method for producing a norbornene derivative, the endo/exo ratio of the configuration of the substituents in the norbornene derivative represented by any of the general formulae (9) to (11) can be made 10/90 to 30/70 (more preferably 15/85 to 25/75). In the present invention, the norbornene derivative is produced in the second step by degrading the Mannich base represented by any of the general formulae (5) to (7), and simultaneously causing a Diels-Alder reaction. In addition, when the heating temperature (reaction temperature) in the second step is set within the above-described preferred range (for example, 60 to 180° C.), the variable endo/exo ratio naturally falls in the above-described range. Note that the norbornene derivative of the present invention has a ketone group, and the ketone group has priority in nomenclature. Hence, although the norbornene derivative is an endo adduct from the viewpoint of the reaction, the norbornene derivative obtained by the reaction is an exo isomer from the viewpoint of nomenclature.

In addition, the thus obtained norbornene derivative represented by any of the general formulae (9) to (11) can be converted into a desired polymer through a ring-opening polymerization, a ring-opening polymerization with a subsequent hydrogenation reaction, an addition polymerization, a radical polymerization, a cationic polymerization, an anionic polymerization, or the like. If necessary, it is also possible to obtain a copolymer by subjecting the norbornene derivative to a copolymerization reaction with any copolymerizable compound. In addition, the polymer synthesized from the norbornene derivative exhibits an excellent transparency, heat resistance and a low water absorbing property, and can be arbitrarily controlled in terms of magnitude of birefringence value and wavelength dispersibility thereof according to its application. For this reason, the polymer synthesized from the norbornene derivative can be suitably applied as a material for forming optical disks, magneto-optical discs, optical lenses (Fθ lenses, pickup lenses, lenses for laser printers, lenses for cameras, and the like), spectacle lenses, optical films/sheets (films for displays, retardation films, polarizing films, protection films for polarizing plates, diffusion films, anti-reflection films, anti-reflection films for EL, liquid-crystal substrates, EL substrates, substrates for electronic paper, substrates for touch panels, PDP front panels, and the like), substrates for transparent electroconductive films, optical fibers, light guide plates, optical cards, optical mirrors, sealing materials for ICs, LSIs, and LEDs, and the like.

EXAMPLES

Hereinafter, the present invention will be described more specifically on the basis of Examples and Comparative Examples. However, the present invention is not limited to Examples below.

Note that, in the following description, the purity of a product obtained in each of Examples and Comparative Examples was measured with a high-performance liquid chromatograph (HPLC, analyzer: "1200 Series" manufactured by Agilent Technologies; column: Chemco Pak (packing: CHEMCOSORB 5-ODS-H, diameter: 4.6, length: 150 mm), solvent: acetonitrile/distilled water/phosphoric acid=70 ml/30 ml/0.1 ml, flow rate: 1 ml/min., detector: UV 254 nm), or with a gas chromatograph (GC, analyzer: "6890N" manufactured by Agilent Technologies; capillary column: "HP-5" manufactured by Agilent Technologies, length: 30 m, inner diameter: 320 μm, film thickness: 0.25 μm). Moreover, the molecular structure of the product obtained in each of Examples and Comparative Examples was identified by measuring $^1$H-NMR and $^{13}$C-NMR of the product obtained in each of the Examples and Comparative Examples in deuterated chloroform, by using a superconducting nuclear magnetic resonance spectrometer (NMR, manufactured by VARIAN, trade name: UNITY INOVA-600).

Example 1

<First Step>
First, to a 100-ml two-necked flask, 6.83 g of a 50% by mass aqueous dimethylamine solution (dimethylamine: 75.9 mmol) was added. Next, to a 100-ml dropping funnel, 8.19 g of a 35% by mass aqueous solution of hydrochloric acid (hydrochloric acid: 78.9 mmol) was added. Subsequently, the dropping funnel is set to the two-necked flask, and the aqueous solution of hydrochloric acid was added dropwise to the aqueous dimethylamine solution under ice-cooling. Thus, dimethylamine hydrochloride was prepared in the two-necked flask. Next, to the two-necked flask, 2.78 g (92.4 mmol) of paraformaldehyde as the formaldehyde derivative and 9.0 g (61.6 mmol) of α-tetralone as the carbonyl compound were further added. Note that the volume of the mixture made of water and paraformaldehyde present in the two-necked flask was 25 mL, and the concentration of hydrochloric acid (HCl) in the mixture was 0.12 mol/L. Subsequently, a bulb condenser was set to the two-necked flask, and then the inside of the two-necked flask was replaced with nitrogen. Thereafter, the two-necked flask was immersed in an oil bath of 90° C., and heated for 4 hours with stirring. Thus, a reaction liquid was obtained.

Note that the thus obtained reaction liquid was subjected to HPLC analysis for components in the reaction liquid. As a result, the conversion of α-tetralone was found to be 99%, and the yield (HPLC yield) of N,N-dimethylaminomethyl-1-tetralone hydrochloride (the Mannich base) was found to be 95%.

<Second Step>
The reaction liquid obtained by carrying out the first step was cooled to 50° C. Next, to the reaction liquid in the two-necked flask, methyl cellosolve (50 ml) as the organic solvent, 1.12 g of a 50% by mass aqueous dimethylamine solution as the base (12.4 mmol: an amount of 4.0 equivalents to the acid in the reaction liquid), and 7.13 g (108 mmol) of cyclopentadiene were added. Thus, a mixture liquid was obtained. Subsequently, the inside of the two-necked flask was replaced with nitrogen, then the two-necked flask was immersed in an oil bath of 120° C., and the mixture liquid was heated for 60 minutes. Note that, when the mixture liquid was heated as described above, the mixture liquid was a light yellow transparent liquid at the initial stage of the reaction, and the mixture liquid turned to a black liquid in about 30 minutes after the start of the heating.

The mixture liquid after heating in this manner was subjected to HPLC analysis. As a result, it was found that spiro [3,4-dihydronaphthalene-2,2'-[5']norbornen]-1-one (TSPNB) was formed, and that the HPLC yield of TSPNB was 85%. From the HPLC analysis, the content of a compound in which $R^5$ and $R^6$ in the general formula (14) were each hydrogen and n therein was 2 was found to be 0% by mass in the heated mixture liquid. Moreover, the content of a dimerization product (dimer) formed by dimerization of the compound in which $R^5$ and $R^6$ in the general formula (14) were each hydrogen and n therein was 2 was found to be 0.8% by mass in the heated mixture liquid. From the results of the HPLC analysis, it has been found that TSPNB can be produced in a sufficiently high selectivity and good yield.

<Extraction Treatment>
The heated mixture liquid was transferred to a 200-ml separatory funnel, then 80 ml of n-heptane was added to the mixture liquid, and liquid separation operation was conducted. As a result, the liquid was separated into two layers, where the upper layer was a n-heptane layer, and the lower layer was a methyl cellosolve layer. After the n-heptane layer and the methyl cellosolve layer were separated from each other as described above, the methyl cellosolve layer being the lower layer was further subjected to an extraction operation with 40 ml of n-heptane, and another n-heptane layer was separated and obtained. Subsequently, the n-heptane layer obtained by the first extraction operation and the n-heptane layer obtained by the second extraction operation were mixed with each other. Thus, a n-heptane extraction liquid was obtained. Thereafter, the n-heptane extraction liquid was washed once with 5% by mass aqueous NaOH (25 ml), subsequently once with 5% by mass aqueous hydrochloric acid (25 ml), further once with 5% by mass aqueous sodium hydrogen carbonate (25 ml), and finally once with saturated aqueous sodium chloride (25 ml). The thus washed n-heptane extraction liquid was dried over anhydrous magnesium sulfate, and then the anhydrous magnesium sulfate was filtered off. Thus, a filtrate was obtained. Subsequently, the obtained filtrate was concentrated by use of an evaporator, and n-heptane was distilled off. Thus, 12.6 g of a crude product (spiro [3,4-dihydronaphthalene-2,2'-[5']norbornen]-1-one (TSPNB)) was obtained (crude yield: 92%). Next, the thus obtained crude product was subjected to Kugelrohr distillation (111° C./0.1 mmHg), and 11.0 g of TSPNB was obtained (yield: 80%, purity: 99.1%).

Figure 2:
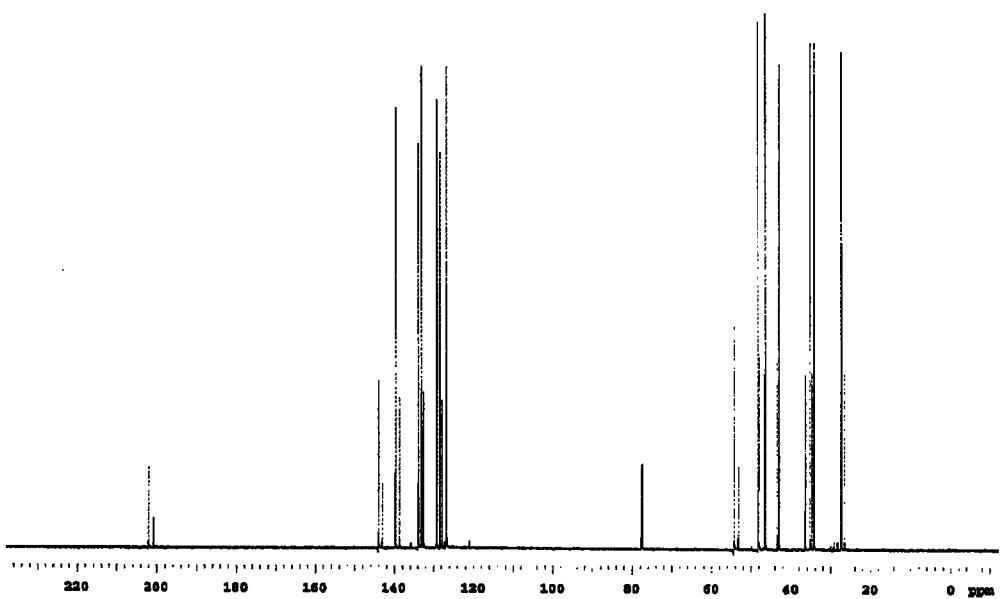
FIG. 2 is a graph of a $^{13}$C-NMR spectrum (CDCl$_3$) of the compound (TSPNB) obtained in Example 1.

To confirm the structure of the thus obtained compound, NMR ($^1$H-NMR and $^{13}$C-NMR) measurement was conducted. FIG. 1 shows $^1$H-NMR obtained by the NMR measurement, and FIG. 2 shows $^{13}$C-NMR obtained by the NMR measurement. As is apparent from the results shown in FIGS. 1 and 2, the obtained compound was confirmed to be TSPNB represented by the following general formula (15), and the ratio (endo/exo) between the endo isomer and the exo isomer was found to be 22/78.

[Chem. 13]

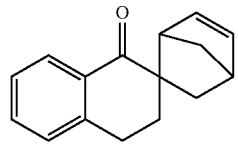

(15)

From these results, it has been found that the method for producing a norbornene derivative of the present invention (Example 1) makes it possible to produce the spiro-type norbornene derivative in a sufficiently high yield.

Examples 2 to 8

Each norbornene derivative was produced in the same manner as in Example 1, except that the kind of the formaldehyde derivative used in the first step and the kind of the organic solvent used in the second step were changed to a formaldehyde derivative and an organic solvent described in the following Table 1, and that the extraction step and the like were modified depending on the kind of the organic solvent as follows. Specifically, first, when the organic solvent was isopropyl alcohol (Examples 2 to 4) or methanol (Example 8), an autoclave was used in the second step. Meanwhile, when the organic solvent was isopropyl alcohol (Examples 2 to 4), the organic solvent was distilled off from the heated mixture liquid in the extraction treatment, and solid-liquid extraction was conducted with n-heptane being added. Thereafter, filtration was conducted. Meanwhile, when the organic solvent was n-butanol (Example 5), the extraction treatment (the liquid-liquid extraction treatment with n-heptane) was conducted, by use of a mixture liquid obtained by distilling off the organic solvent from the heated mixture liquid before the extraction treatment, and adding 40 ml of water thereto. Note that, when the organic solvent was isopropyl alcohol (Examples 2 to 4), and when the organic solvent was n-butanol (Example 5), the organic solvents were distilled off, because the organic solvents are miscible with n-heptane used for the separation by extraction.

To confirm the structure of the norbornene derivative thus obtained in each of Examples 2 to 8, NMR measurement was conducted. As a result, all the norbornene derivatives obtained in the examples were confirmed to be the norbornene derivative (TSPNB) represented by the general formula (15). In addition, Table 1 shows the results of HPLC measurement (the yield of N,N-dimethylaminomethyl-1-tetralone hydrochloride obtained in the first step and the yield of the norbornene derivative (TSPNB) obtained in the second step).

Next, a bulb condenser was set to the three-necked flask, and then the inside atmosphere of the three-necked flask was replaced with nitrogen. Thereafter, the three-necked flask was immersed in an oil bath of 100° C., and the mixture liquid was stirred for 60 minutes with heating. After thus stirred, the mixture liquid was cooled with ice to 25° C., and was washed twice with diethyl ether (twice with 30 ml each). Subsequently, the thus washed mixture liquid was allowed to stand one day and one night (24 hours). White crystals formed in the mixture liquid were separated by filtration, and washed with acetone. The thus obtained white crystals were vacuum dried. Thus, 12.9 g of N,N-dimethylaminomethyl-1-tetralone hydrochloride was obtained (yield: 11%). Note that the thus obtained compound was subjected to NMR measurement. As a result, it was found that a purity of N,N-dimethylaminomethyl-1-tetralone hydrochloride was 85.7%, and that 14.3% of dimethylamine hydrochloride was included as a by-product.

Next, a mixture of 2.4 g (0.01 mol) of the above N,N-dimethylaminomethyl-1-tetralone hydrochloride, 100 ml of ethanol, 13.2 g (0.1 mol) of cyclopentadiene was fed into an autoclave. The thus obtained reaction mixture liquid was heated at 120° C. for 4 hours. The reaction mixture liquid after heating in this manner was subjected to HPLC analysis. As a result, the HPLC yield of spiro[3,4-dihydronaphthalene-2,2'-[5']norbornen]-1-one (TSPNB) was found to be 87%. From the results, the total yield of TSPNB was found to be 9.6%.

TABLE 1

| | First step | | | Second step | |
|---|---|---|---|---|---|
| | Formaldehyde derivative | Concentration of acid | HPLC yield of Mannich base | Organic solvent | HPLC yield of Norbornene derivative |
| Example 2 | Aqueous formalin solution (37% by mass) | 0.12 mol/L | 93% | Isopropyl alcohol | 90% |
| Example 3 | Paraformaldehyde | 0.12 mol/L | 94% | Isopropyl alcohol | 88% |
| Example 4 | 1,3-Dioxolane | 0.12 mol/L | 92% | Isopropyl alcohol | 88% |
| Example 5 | Paraformaldehyde | 0.12 mol/L | 95% | n-Butanol | 89% |
| Example 6 | Paraformaldehyde | 0.12 mol/L | 95% | Propylene glycol | 88% |
| Example 7 | Paraformaldehyde | 0.12 mol/L | 95% | Propylene glycol monomethyl ether | 87% |
| Example 8 | Paraformaldehyde | 0.12 mol/L | 95% | Methanol | 80% |

As is apparent from the results shown in Table 1, it has been found that, when N,N-dimethylaminomethyl-1-tetralone hydrochloride (the Mannich base) is produced in the first step under acidic conditions as shown in Table 1, the Mannich base can be produced in a sufficiently high yield. Moreover, it has been found that the method for producing a norbornene derivative of the present invention (Example 2 to 8) where the first step and the second step are carried out makes it possible to produce the norbornene derivative in a sufficiently high yield.

Comparative Example 1

With reference to the methods described in "Bulletin de la Societe Chimique de France (5)" published in 1966, Pages 1693 to 1698, and in "Arch. pharm.", vol. 275, published in 1937, Pages 54 to 62, the norbornene derivative was produced as follows.

Specifically, first, a mixture liquid was obtained by feeding 73 g (0.5 mol) of α-tetralone, 47.3 g (0.55 mol) of a 37% by mass aqueous formalin solution, and 45 g (0.55 mol) of dimethylamine hydrochloride to a 500-ml three-necked flask.

From these results, it has been found that, by the conventional methods for producing a norbornene derivative as described in Bulletin de la Societe Chimique de France (5) and Arch. pharm., the yield of N,N-dimethylaminomethyl-1-tetralone hydrochloride, which is the reaction intermediate, is insufficient, and the yield of the finally obtained norbornene derivative is insufficient.

Comparative Example 2

First, 6.83 g of a 50% by mass aqueous dimethylamine solution (dimethylamine: 75.9 mmol) was added to a 100-ml two-necked flask. Next, 8.19 g of a 35% by mass aqueous solution of hydrochloric acid (hydrochloric acid: 78.9 mmol) was added to a 100-ml dropping funnel. Subsequently, the dropping funnel was set to the two-necked flask, and then the aqueous solution of hydrochloric acid was added dropwise to the aqueous dimethylamine solution under ice-cooling. Thus, dimethylamine hydrochloride was prepared in the two-necked flask. Next, 2.78 g (92.4 mmol) of paraformaldehyde as the formaldehyde derivative and 9.0 g (61.6 mmol) of α-tetralone as the carbonyl compound were further added to the two-necked flask. Note that the volume of the mixture made of water and paraformaldehyde present in the two-necked flask was 25 mL, and the concentration of hydrochloric acid (HCl) in the mixture was 0.12 mol/L. Subsequently, a bulb condenser was set to the two-necked flask, and then the inside of the two-necked flask was replaced with nitrogen. Thereafter, the two-necked flask was immersed in an oil bath of 90° C., and heated for 4 hours with stirring. Thus, a reaction liquid was obtained. Note that the thus obtained reaction liquid was subjected to HPLC analysis for components in the reaction liquid. As a result, the conversion of α-tetralone was found to be 99%, and the yield (HPLC yield) of N,N-dimethylaminomethyl-1-tetralone hydrochloride (the Mannich base) was found to be 95%.

Next, the reaction liquid in the two-necked flask was cooled to 50° C., and then n-butanol (50 ml) and 7.13 g (108 mmol) of cyclopentadiene were added to the reaction liquid. Thus, a mixture liquid was obtained. Subsequently, the inside of the two-necked flask was replaced with nitrogen, then the two-necked flask was immersed in an oil bath of 120° C., and the mixture liquid was heated for 60 minutes. Note that, when the mixture liquid was heated as described above, the mixture liquid was a light yellow transparent liquid at the initial stage of the reaction, and turned to a brown solution in about 30 minutes after the start of the heating. The thus heated mixture liquid was subjected to HPLC analysis. As a result, the HPLC yield of spiro[3,4-dihydronaphthalene-2,2'-[5']norbornen]-1-one (TSPNB) was 0%.

From these results, it has been found that, even when the reaction liquid obtained in the first step according to the present invention is used, the norbornene derivative cannot be produced sufficiently, if no base is introduced at the time of causing the reaction between cyclopentadiene and the Mannich base.

Example 9

<First Step>

First, to a 100-ml two-necked flask, 6.83 g of a 50% by mass aqueous dimethylamine solution (dimethylamine: 75.9 mmol) was added. Next, to a 100-ml dropping funnel, 8.19 g of a 35% by mass aqueous solution of hydrochloric acid (78.9 mmol) was added. Subsequently, the dropping funnel was set to the two-necked flask, and the aqueous solution of hydrochloric acid was added dropwise to the aqueous dimethylamine solution under ice-cooling. Thus, dimethylamine hydrochloride was prepared in the two-necked flask. Next, to the two-necked flask, 2.78 g (92.4 mmol) of paraformaldehyde as the formaldehyde derivative and 8.14 g (61.6 mmol) of 1-indanone as the carbonyl compound were further added. Note that the volume of the mixture made of water and paraformaldehyde present in the two-necked flask was 24 mL, and the concentration of hydrochloric acid (HCl) in the mixture was 0.12 mol/L. Subsequently, a bulb condenser was set to the two-necked flask, and then the inside of the two-necked flask was replaced with nitrogen. Thereafter, the two-necked flask was immersed in an oil bath of 90° C., and heated for 3 hours with stirring. Thus a reaction liquid was obtained.

Note that the thus obtained reaction liquid was subjected to HPLC analysis for components in the reaction liquid. As a result, the conversion of 1-indanone was found to be 99%, and the HPLC yield of N,N-dimethylaminomethyl-1-indanone hydrochloride was found to be 94%.

<Second Step>

The reaction liquid obtained by carrying out the first step was cooled to 50° C. Next, to the reaction liquid in the two-necked flask, n-butanol (50 ml) as the organic solvent, 1.12 g of a 50% by mass aqueous dimethylamine solution as the base (12.4 mmol: an amount of 4.0 equivalents to the acid in the reaction liquid), and 7.13 g (108 mmol) of cyclopentadiene were added. Thus, a mixture liquid was obtained. Subsequently, the inside of the two-necked flask was replaced with nitrogen, then the two-necked flask was immersed in an oil bath of 120° C., and the mixture liquid was heated for 60 minutes.

The mixture liquid after heating in this manner was subjected to HPLC analysis. As a result, it was found that spiro[indane-2,2'-[5']norbornen]-1-one (ISPNB) was formed, and that the HPLC yield of ISPNB was 89%.

<Extraction Treatment>

After n-butanol was distilled off from the heated mixture liquid with an evaporator, ion-exchanged water (40 ml) and n-heptane (60 ml) were added thereto. Thus, a second mixture liquid was obtained. Next, 200 ml of the obtained second mixture liquid was transferred to a separatory funnel, and extraction operations were conducted. Then, the aqueous layer was discarded. After that, the obtained n-heptane extraction liquid was washed once with 5% by mass aqueous NaOH (25 ml), washed once with 5% by mass aqueous hydrochloric acid (25 ml), further washed once with 5% aqueous sodium hydrogen carbonate (25 ml), and finally washed once with saturated aqueous sodium chloride (25 ml). The thus washed n-heptane extraction liquid was dried over anhydrous magnesium sulfate, and the anhydrous magnesium sulfate was filtered off. Thus, a filtrate was obtained. Subsequently, the obtained filtrate was concentrated by use of an evaporator, and n-heptane was distilled off. Thus, 11.6 g of a crude product (ISPNB) was obtained (crude yield: 89%). Next, the thus obtained crude product was subjected to Kugelrohr distillation (boiling point: 117° C./0.1 mmHg), and 10.5 g of ISPNB was obtained (yield: 81%, purity: 99.0%).

Figure 3:
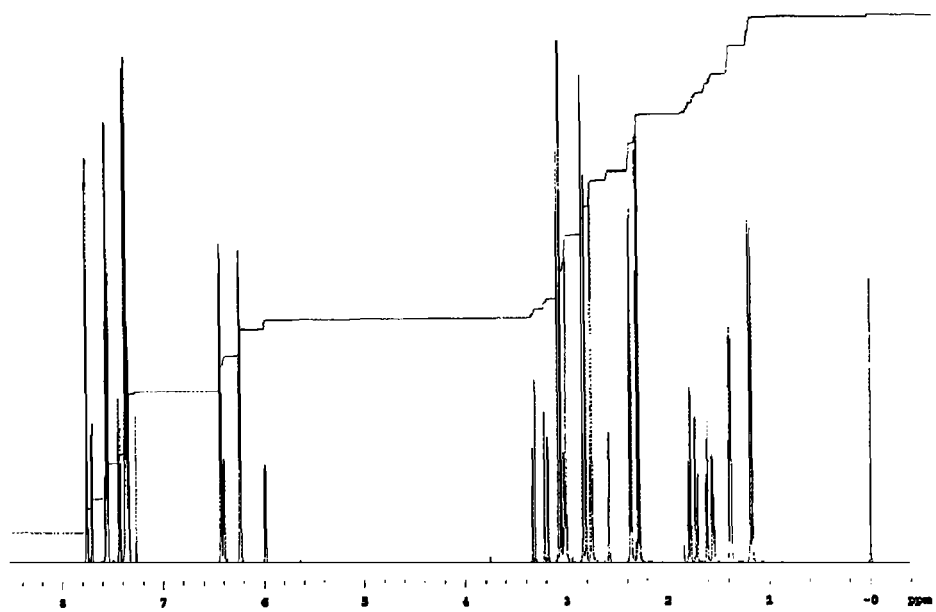
FIG. 3 is a graph of a $^1$H-NMR spectrum (CDCl$_3$) of a compound (ISPNB) obtained in Example 9.
Figure 4:
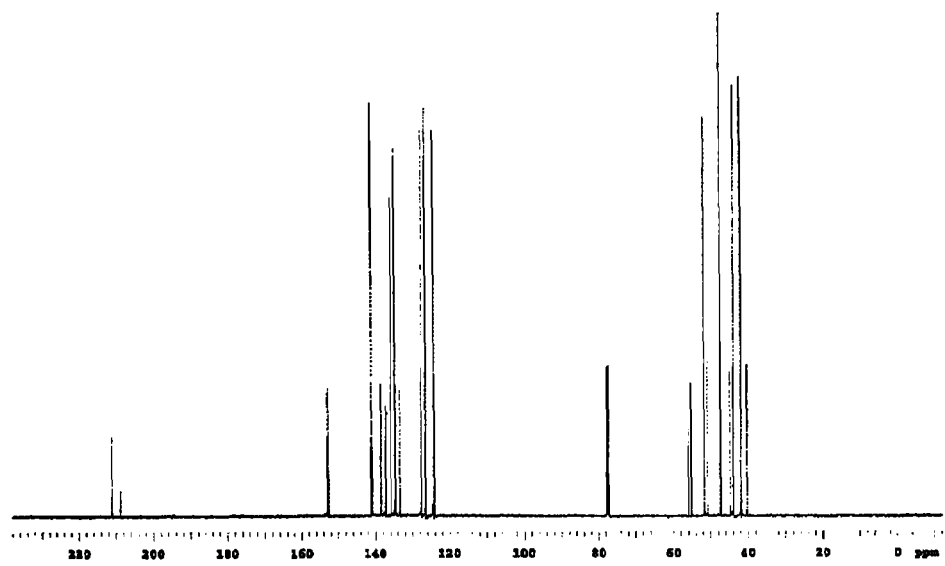
FIG. 4 is a graph of a $^{13}$C-NMR spectrum (CDCl$_3$) of the compound (ISPNB) obtained in Example 9.

To confirm the structure of the thus obtained compound, NMR ($^1$H-NMR and $^{13}$C-NMR) measurement was conducted. FIG. 3 shows $^1$H-NMR obtained by the NMR measurement, and FIG. 4 shows $^{13}$C-NMR obtained by the NMR measurement. As is apparent from the results shown in FIG. 3 and FIG. 4, the obtained compound was confirmed to be ISPNB represented by the following general formula (16), and the ratio (endo/exo) between the endo isomer and the exo isomer was found to be 27/73.

[Chem. 14]

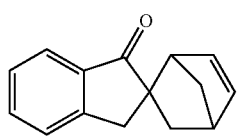

(16)

Example 10

<First Step>

First, to a 100-ml two-necked flask, 6.83 g (75.9 mmol) of a 50% by mass aqueous dimethylamine solution was added. Next, to a 100-ml dropping funnel, 8.19 g (78.9 mmol) of 35% by mass hydrochloric acid was added. Subsequently, the dropping funnel was set to the two-necked flask, and the aqueous solution of hydrochloric acid was added dropwise to the aqueous dimethylamine solution under ice-cooling. Thus, dimethylamine hydrochloride was prepared in the two-necked flask. Next, to the two-necked flask, 9.13 g (123.2 mmol) of 1,3-dioxolane as the formaldehyde derivative and 9.87 g (61.6 mmol) of benzosuberone as the carbonyl compound were further added. Note that the volume of the mixture made of water and 1,3-dioxolane present in the two-necked flask was 34 mL, and the concentration of hydrochloric acid (HCl) in the mixture was 0.09 mol/L. Subsequently, a bulb condenser was set to the two-necked flask, and then the inside of the two-necked flask was replaced with nitrogen. Thereafter, the two-necked flask was immersed in an oil bath of 90° C., and heated for 6 hours with stirring. Thus, a reaction liquid was obtained.

Note that the thus obtained reaction liquid was subjected to HPLC analysis for components in the reaction liquid. As a result, the conversion of benzosuberone was found to be 98%, and the HPLC yield of N,N-dimethylaminomethyl-1-benzosuberone hydrochloride was found to be 89%.

<Second Step>

The reaction liquid obtained by carrying out the first step was cooled to 50° C. Next, to the reaction liquid in the two-necked flask, n-butanol (50 ml) as the organic solvent, 1.12 g of a 50% by mass aqueous dimethylamine solution as the base (12.4 mmol: an amount of 4.0 equivalents to the acid in the reaction liquid), and 7.13 g (108 mmol) of cyclopentadiene were added. Thus, a mixture liquid was obtained. Subsequently, the inside of the two-necked flask was replaced with nitrogen, then the two-necked flask was immersed in an oil bath of 120° C., and the mixture liquid was heated for 90 minutes.

The mixture liquid after heating in this manner was subjected to HPLC analysis. As a result, it was found that spiro[benzosuberone-2,2'-[5']norbornen]-1-one (BSPNB) was formed in the mixture liquid, and that the HPLC yield of the BSPNB was 85%.

<Extraction Treatment>

After n-butanol was distilled off from the heated mixture liquid with an evaporator, ion-exchanged water (40 ml) and n-heptane (60 ml) were added thereto. Thus, a second mixture liquid was obtained. Next, 200 ml of the obtained second mixture liquid was transferred to a separatory funnel, and extraction operations were conducted. Then, the aqueous layer was discarded. After that, the obtained n-heptane extraction liquid was washed once with 5% by mass aqueous NaOH (25 ml), washed once with 5% by mass aqueous hydrochloric acid (25 ml), further washed once with 5% aqueous sodium hydrogen carbonate (25 ml), and finally washed once with saturated aqueous sodium chloride (25 ml). The thus washed n-heptane extraction liquid was dried over anhydrous magnesium sulfate, and the anhydrous magnesium sulfate was filtered off. Thus, a filtrate was obtained. Subsequently, the obtained filtrate was concentrated by use of an evaporator, and n-heptane was distilled off. Thus, 13.4 g of a crude product (BSPNB) was obtained (crude yield: 91%). Next, the thus obtained crude product was subjected to Kugelrohr distillation (boiling point: 135° C./0.1 mmHg). Thus, 10.8 g of BSPNB was obtained (yield: 74%, purity: 95.0%).

To confirm the structure of the thus obtained compound, NMR ($^1$H-NMR and $^{13}$C-NMR) measurement was conducted. As a result, the obtained compound was confirmed to be BSPNB represented by the following general formula (17), and the ratio (endo/exo) between the endo isomer and the exo isomer was found to be 20/80.

[Chem. 15]

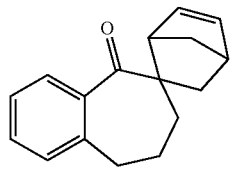

(17)

Example 11

<First Step>

First, to a 100-ml two-necked flask, 6.83 g of a 50% by mass aqueous dimethylamine solution (dimethylamine: 75.9 mmol) was added. Next, to a 100-ml dropping funnel, 8.19 g (78.9 mmol) of a 35% by mass aqueous solution of hydrochloric acid was added. Subsequently, the dropping funnel was set to the two-necked flask, and the aqueous solution of hydrochloric acid was added dropwise to the aqueous dimethylamine solution under ice-cooling. Thus, dimethylamine hydrochloride was prepared in the two-necked flask. Next, to the two-necked flask, 2.78 g (92.4 mmol) of paraformaldehyde as the formaldehyde derivative and 5.18 g (61.6 mmol) of cyclopentanone as the carbonyl compound were further added. Note that the volume of the mixture made of water and paraformaldehyde present in the two-necked flask was 23 mL, and the concentration of hydrochloric acid (HCl) in the mixture was 0.13 mol/L. Subsequently, a bulb condenser was set to the two-necked flask, and then the inside of the two-necked flask was replaced with nitrogen. Thereafter, the two-necked flask was immersed in an oil bath of 90° C., and heated for 3 hours with stirring. Thus, a reaction liquid was obtained. The thus obtained reaction liquid was subjected to GC analysis. As a result, the conversion of cyclopentanone was found to be 99%.

<Second Step>

The reaction liquid obtained by carrying out the first step was cooled to 50° C. Next, to the reaction liquid in the two-necked flask, n-butanol (50 ml) as the organic solvent, 1.12 g of a 50% by mass aqueous dimethylamine solution as the base (12.4 mmol: an amount of 4.0 equivalents to the acid in the reaction liquid), and 7.13 g (108 mmol) of cyclopentadiene were added. Thus, a mixture liquid was obtained. Subsequently, the inside of the two-necked flask was replaced with nitrogen, then the two-necked flask was immersed in an oil bath of 120° C., and the mixture liquid was heated for 90 minutes.

<Extraction Treatment>

After n-butanol was distilled off from the heated mixture liquid with an evaporator, ion-exchanged water (40 ml) and n-heptane (60 ml) were added thereto. Thus, a second mixture liquid was obtained. Next, 200 ml of the obtained second mixture liquid was transferred to a separatory funnel, and extraction operations were conducted. Then, the aqueous layer was discarded. After that, the obtained n-heptane extraction liquid was washed once with 5% by mass aqueous NaOH (25 ml), washed once with 5% by mass aqueous hydrochloric acid (25 ml), further washed once with 5% aqueous sodium hydrogen carbonate (25 ml), and finally washed once with saturated aqueous sodium chloride (25 ml). The thus washed n-heptane extraction liquid was dried over anhydrous magnesium sulfate, and the anhydrous magnesium sulfate was filtered off. Thus, a filtrate was obtained. Subsequently, the obtained filtrate was concentrated by use of an evaporator, and n-heptane was distilled off. Thus, 9.9 g of a crude product, (spiro[cyclopentane-2,2'-[5']norbornen]-1-one (PSPNB)), was obtained (crude yield: 99%). Next, the thus obtained crude product was subjected to Kugelrohr distillation (boiling point: 50° C./1 mmHg). Thus, 6.1 g of PSPNB was obtained (yield: 61%). Note that, when distillation was conducted further, 3.7 g of 5-norbornene-2-spiro-2'-cyclopentanone-5'-spiro-2''-5''-norbornene was identified as a by-product (boiling point: 105° C./0.1 mmHg).

To confirm the structure of the thus obtained compound, NMR ($^1$H-NMR and $^{13}$C-NMR) measurement was conducted. As a result, the obtained compound was confirmed to be PSPNB represented by the following general formula (18), and the ratio (endo/exo) between the endo isomer and the exo isomer was found to be 11/89.

[Chem. 16]

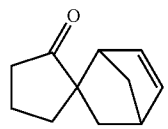

(18)

Example 12

<First Step>

First, to a 100-ml two-necked flask, 6.83 g of a 50% by mass aqueous dimethylamine solution (dimethylamine: 75.9 mmol) was added. Next, to a 100-ml dropping funnel, 8.19 g (78.9 mmol) of a 35% by mass aqueous solution of hydrochloric acid was added. Subsequently, the dropping funnel was set to the two-necked flask, and the aqueous solution of hydrochloric acid was added dropwise to the aqueous dimethylamine solution under ice-cooling. Thus, dimethylamine hydrochloride was prepared in the two-necked flask. Next, to the two-necked flask, 2.78 g (92.4 mmol) of paraformaldehyde as the formaldehyde derivative and 6.05 g (61.6 mmol) of cyclohexanone as the carbonyl compound were further added. Note that the volume of the mixture made of water and paraformaldehyde present in the two-necked flask was 24 mL, and the concentration of hydrochloric acid (HCl) in the mixture was 0.12 mol/L. Subsequently, a bulb condenser was set to the two-necked flask, and then the inside of the two-necked flask was replaced with nitrogen. Thereafter, the two-necked flask was immersed in an oil bath of 90° C., and heated for 2 hours with stirring. Thus, a reaction liquid was obtained. The thus obtained reaction liquid was subjected to GC analysis. As a result, the conversion of cyclohexanone was found to be 100%.

<Second Step>

The reaction liquid obtained by carrying out the first step was cooled to 50° C. Next, to the reaction liquid in the two-necked flask, n-butanol (50 ml) as the organic solvent, 1.12 g of a 50% by mass aqueous dimethylamine solution as the base (12.4 mmol: an amount of 4.0 equivalents to the acid in the reaction liquid), and 7.13 g (108 mmol) of cyclopentadiene were further added. Thus, a mixture liquid was obtained. Subsequently, the inside of the two-necked flask was replaced with nitrogen, then the two-necked flask was immersed in an oil bath of 120° C., and the mixture liquid was heated for 90 minutes.

<Extraction Treatment>

After n-butanol was distilled off from the heated mixture liquid with an evaporator, ion-exchanged water (40 ml) and n-heptane (60 ml) were added thereto. Thus, a second mixture liquid was obtained. Next, 200 ml of the obtained second mixture liquid was transferred to a separatory funnel, and extraction operations were conducted. Then, the aqueous layer was discarded. After that, the obtained n-heptane extraction liquid was washed once with 5% by mass aqueous NaOH (25 ml), washed once with 5% by mass aqueous hydrochloric acid (25 ml), further washed once with 5% aqueous sodium hydrogen carbonate (25 ml), and finally washed once with saturated aqueous sodium chloride (25 ml). The thus washed n-heptane extraction liquid was dried over anhydrous magnesium sulfate, and the anhydrous magnesium sulfate was filtered off. Thus, a filtrate was obtained. Subsequently, the obtained filtrate was concentrated by use of an evaporator, and n-heptane was distilled off. Thus, 10.1 g of a crude product (spiro[cyclohexane- 2,2'-[5']norbornen]-1- one (CSPNB)) was obtained (crude yield: 93%). Next, the thus obtained crude product was subjected to Kugelrohr distillation (boiling point: 70° C./0.5 mmHg), and 6.5 g of CSPNB was obtained (yield: 60%). Note that, when distillation was further conducted, 3.0 g of 5-norbornene-2-spiro-2'-cyclohexanone-6'-spiro-2''-5''-norbornene was identified as a by-product (boiling point: 110° C./0.1 mmHg).

Figure 5:
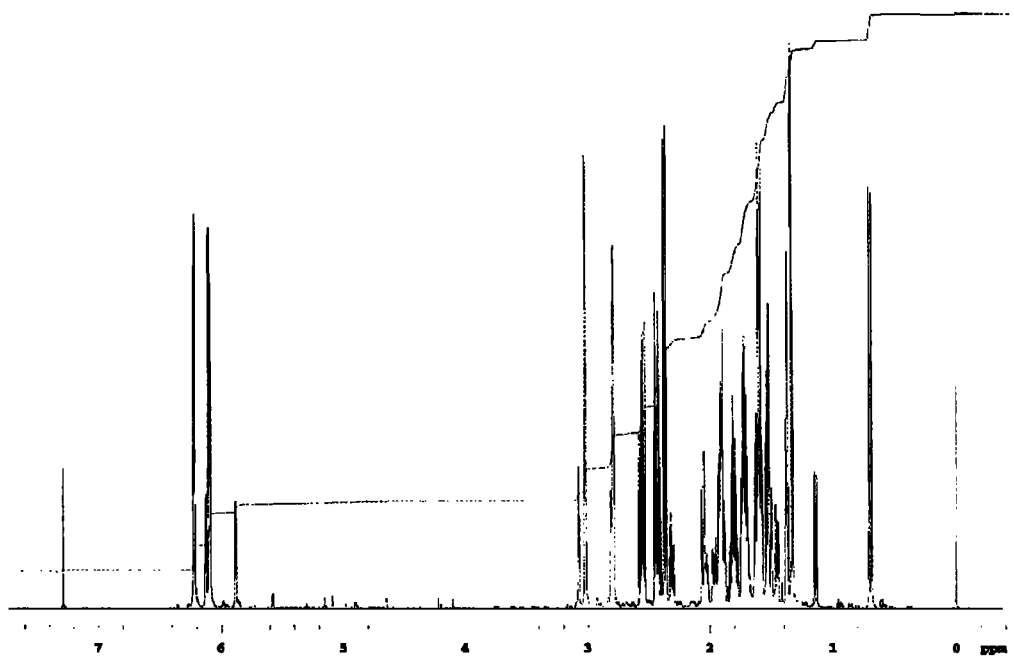
FIG. 5 is a graph of a $^1$H-NMR spectrum (CDCl$_3$) of a compound (CSPNB) obtained in Example 12.
Figure 6:
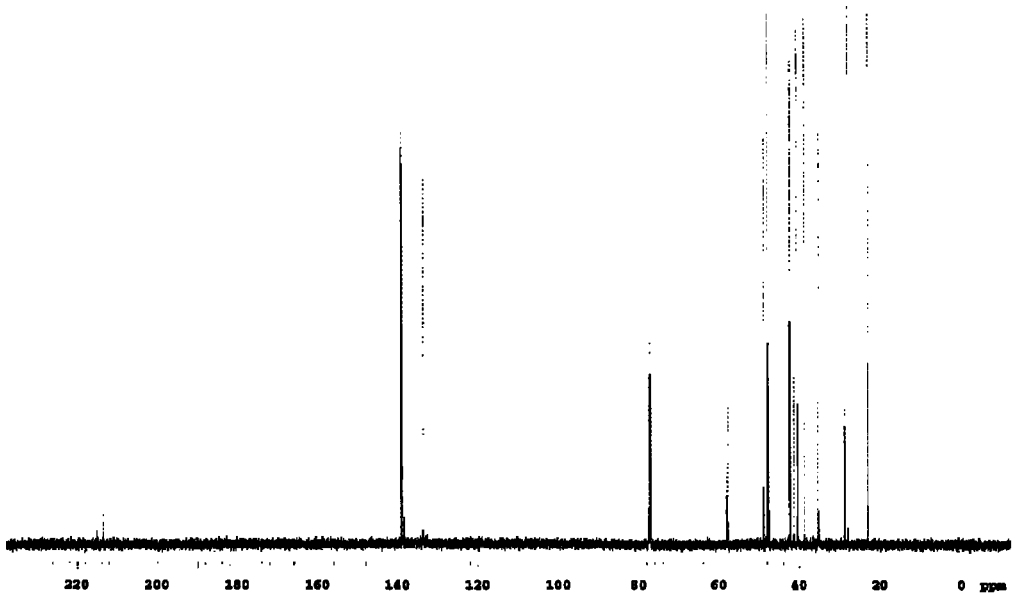
FIG. 6 is a graph of a $^{13}$C-NMR spectrum (CDCl$_3$) of the compound (CSPNB) obtained in Example 12.

To confirm the structure of the thus obtained compound, NMR ($^1$H-NMR and $^{13}$C-NMR) measurement was conducted. FIG. 5 shows $^1$H-NMR obtained by the NMR measurement, and FIG. 6 shows $^{13}$C-NMR obtained by the NMR measurement. As is apparent from the results shown in FIG. 5 and FIG. 6, the obtained compound was confirmed to be CSPNB represented by the following general formula (19), and the ratio (endo/exo) between the endo isomer and the exo isomer was found to be 22/78.

[Chem. 17]

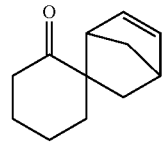

(19)

Example 13

<First Step>

First, to a 100-ml two-necked flask, 6.83 g of a 50% by mass aqueous dimethylamine solution (dimethylamine: 75.9 mmol) was added. Next, to a 100-ml dropping funnel, 8.19 g of a 35% by mass aqueous solution of hydrochloric acid (hydrochloric acid: 78.9 mmol) was added. Subsequently, the dropping funnel was set to the two-necked flask, and the aqueous solution of hydrochloric acid was added dropwise to the aqueous dimethylamine solution under ice-cooling. Thus, dimethylamine hydrochloride was prepared in the two-necked flask. Next, to the two-necked flask, 2.78 g (92.4 mmol) of paraformaldehyde as the formaldehyde derivative and 7.40 g (61.6 mmol) of acetophenone as the carbonyl compound were further added. Note that the volume of the mixture made of water and paraformaldehyde present in the two-necked flask was 25 mL, and the concentration of hydrochloric acid (HCl) in the mixture was 0.12 mol/L. Subsequently, a bulb condenser was set to the two-necked flask, and then the inside of the two-necked flask was replaced with nitrogen. Subsequently, a bulb condenser was set to the two-necked flask, and then the inside of the two-necked flask was replaced with nitrogen. Thereafter, the two-necked flask was immersed in an oil bath of 90° C., and heated for 8 hours with stirring. Thus, a reaction liquid was obtained. The thus obtained reaction liquid was subjected to HPLC analysis for components in the reaction liquid. As a result, the conversion of acetophenone was 98%.

<Second Step>

The reaction liquid obtained by carrying out the first step was cooled to 50° C. Next, to the reaction liquid in the two-necked flask, n-butanol (50 ml) as the organic solvent, 1.12 g of a 50% by mass aqueous dimethylamine solution as the base (12.4 mmol: an amount of 4.0 equivalents to the acid in the reaction liquid), and 7.13 g (108 mmol) of cyclopentadiene were added. Thus, a mixture liquid was obtained. Subsequently, the inside of the two-necked flask was replaced with nitrogen, then the two-necked flask was immersed in an oil bath of 130° C., and the mixture liquid was heated for 90 minutes.

<Extraction Treatment>

After n-butanol was distilled off from the heated mixture liquid with an evaporator, ion-exchanged water (40 ml) and n-heptane (60 ml) were added thereto. Thus, a second mixture liquid was obtained. Next, 200 ml of the obtained second mixture liquid was transferred to a separatory funnel, and extraction operations were conducted. Thus, the aqueous layer was discarded. After that, the obtained n-heptane extraction liquid was washed once with 5% by mass aqueous NaOH (15 ml), washed once with 5% by mass aqueous hydrochloric acid (15 ml), and further washed tree times with saturated aqueous sodium chloride (10 ml). The thus washed n-heptane extraction liquid was dried over anhydrous magnesium sulfate, and the anhydrous magnesium sulfate was filtered off. Thus, a filtrate was obtained. Subsequently, the obtained filtrate was concentrated by use of an evaporator, and n-heptane was distilled off. Thus, 11.0 g of a crude product (2-benzoyl-5-norbornene (BNB)) was obtained (crude yield: 90%). Next, the thus obtained crude product was subjected to Kugelrohr distillation (boiling point: 110° C./0.1 mmHg), and 9.8 g of BNB was obtained (yield: 810).

Figure 7:
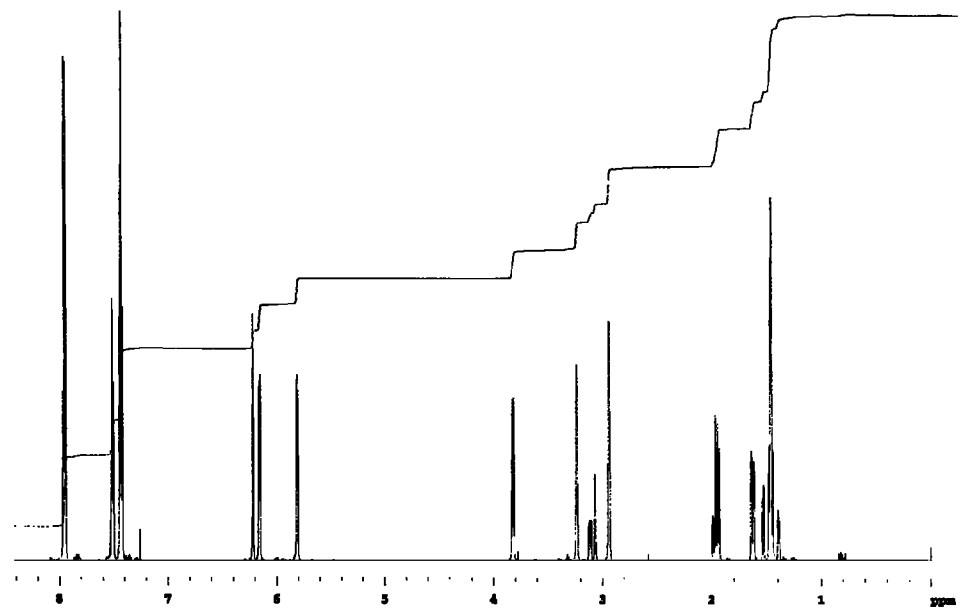
FIG. 7 is a graph of a $^1$H-NMR spectrum (CDCl$_3$) of a compound (BNB) obtained in Example 13.
Figure 8:
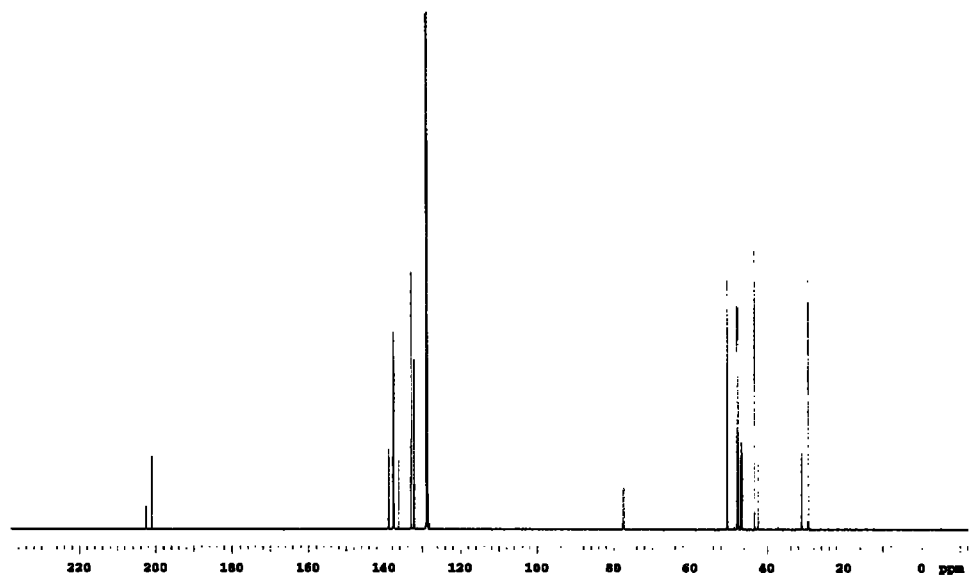
FIG. 8 is a graph of a $^{13}$C-NMR spectrum (CDCl$_3$) of the compound (BNB) obtained in Example 13.

To confirm the structure of the thus obtained compound, NMR ($^1$H-NMR and $^{13}$C-NMR) measurement was conducted. FIG. 7 shows $^1$H-NMR obtained by the NMR measurement, and FIG. 8 shows $^{13}$C-NMR obtained by the NMR measurement. As is apparent from the results shown in FIG. 7 and FIG. 8, the obtained compound was confirmed to be BNB represented by the following general formula (20), and the ratio (endo/exo) between the endo isomer and the exo isomer was found to be 25/75.

[Chem. 18]

(20)

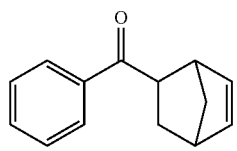

From these results, it has been found out that the method for producing a norbornene derivative of the present invention (Examples 9 to 13) makes it possible to produce spiro-type norbornene derivatives in sufficiently high yields.

Example 14

A norbornene derivative (TSPNB) was obtained in the same manner as in Example 1, except that an extraction treatment described below was conducted instead of the above-described extraction treatment.

Specifically, as the extraction and separation treatment, the heated mixture liquid obtained in the second step was first transferred to a 200-ml separatory funnel, and then 80 ml of n-heptane was added to the mixture liquid. As a result, the mixture was separated into two layers, where the upper layer was a n-heptane layer and the lower layer was a methyl cellosolve layer. After the n-heptane layer and the methyl cellosolve layer were thus separated from each other, the methyl cellosolve layer being the lower layer was further subjected to another extraction operation with 40 ml of n-heptane. Thus, another n-heptane layer was obtained. Subsequently, the n-heptane layer obtained by the first extraction operation and the n-heptane layer obtained by the second extraction operation were mixed together. Thus, a n-heptane extraction liquid was obtained. Subsequently, the thus obtained n-heptane extraction liquid was dried over anhydrous magnesium sulfate, and then the anhydrous magnesium sulfate was filtered off. Thus, a filtrate was obtained. Subsequently, the obtained filtrate was concentrated by use of an evaporator, and n-heptane was distilled off. Thus, 14.8 g of a crude product (spiro[3,4-dihydronaphthalene-2,2'-[5']norbornen]-1-one (TSPNB)) was obtained (crude yield: 108%). Next, the thus obtained crude product was subjected to Kugelrohr distillation (150° C. to 155° C./0.1 mmHg), and 9.0 g of TSPNB was obtained (yield: 66%, purity: 91.0%, by-products: 4.3% of vinyl ketone and 4.7% of vinyl ketone dimer).

From these results, it has been found that the method for producing a norbornene derivative of the present invention (Example 14) makes it possible to produce a spiro-type norbornene derivative in a sufficiently high yield. In addition, a comparison of Example 1 with Example 14 showed that the yield and the purity were more improved in a case where the washing with the aqueous alkaline solution and the aqueous acid solution was conducted after the n-heptane extraction liquid was obtained (Example 1) than in a case where no such washing was conducted (Example 14). Considering that the temperature of the Kugelrohr distillation was elevated in Example 14 by about 40° C., and the pyrolysis temperature (retro-Diels-Alder reaction temperature) of TSPNB is about 120° C., it is presumed that these results were attributable to degradation of TSPNB into the vinyl ketone and cyclopentadiene during the distillation. From these results, it has been found that a further high yield can be achieved by carrying out washing with the aqueous alkaline solution and the aqueous acid solution after the extraction liquid is obtained.

INDUSTRIAL APPLICABILITY

As described above, according to the present invention, it is possible to provide a method for producing a norbornene derivative, which makes it possible to produce a norbornene derivative having a predetermined structure such as a spiro-type norbornene derivative in a sufficiently high yield. Accordingly, the method for producing a norbornene derivative of the present invention is useful as, for example, a method capable of efficiently producing a norbornene derivative having a specific structure, which can be used as a raw material compound for optical disks, magneto-optical discs, optical lenses, spectacle lenses, optical films, optical sheets, and the like.

The invention claimed is:

1. A method for producing a norbornene derivative, comprises a first step of forming a Mannich base by reacting a carbonyl compound and an amine compound with each other in an acidic solvent, to thereby obtain a reaction liquid comprising the Mannich base in the acidic solvent, wherein the acidic solvent comprises a formaldehyde derivative and 0.01 mol/L or more of an acid represented by a formula: HX wherein X represents any selected from the group consisting of F, Cl, Br, I, $CH_3COO$, $CF_3COO$, $CH_3SO_3$, $CF_3SO_3$, $C_6H_5SO_3$, $CH_3C_6H_4SO_3$, $HOSO_3$, and $H_2PO_4$, the carbonyl compound is represented by any of the following general formulae (1) to (3):

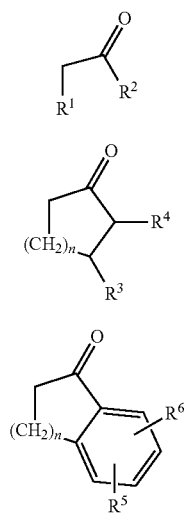

wherein the formulae (1) to (3), $R^1$, $R^2$, $R^3$, $R^4$, $R^5$, and $R^6$ each independently represent any one selected from the group consisting of a hydrogen atom, linear chain saturated hydrocarbon groups having 1 to 10 carbon atoms, branched chain saturated hydrocarbon groups having 3 to 10 carbon atoms, saturated cyclic hydrocarbon groups having 3 to 8 carbon atoms, aryl groups having 6 to 12 carbon atoms, aralkyl groups having 7 to 13 carbon atoms, alkoxy groups having 1 to 10 carbon atoms, a fluorine atom, a chlorine atom, and a bromine atom, and n represents an integer of any of 0 to 4, the amine compound is represented by the following general formula (4):

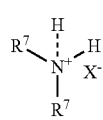

wherein the formula (4), $R^7$s each independently represent any one selected from the group consisting of linear chain saturated hydrocarbon groups having 1 to 20 carbon atoms, branched chain saturated hydrocarbon groups having 3 to 20 carbon atoms, saturated cyclic hydrocarbon groups having 3 to 20 carbon atoms, saturated hydrocarbon groups having a hydroxyl group and 1 to 10 carbon atoms, the two $R^7$s may be bonded to each other to form any one ring selected from the group consisting of a pyrrolidine ring, a piperidine ring, a piperazine ring, and a morpholine ring, and $X^-$ represents any one selected from the group consisting of $F^-$, $Cl^-$, $Br^-$, $I^-$, $CH_3COO^-$, $CF_3COO^-$, $CH_3SO_3^-$, $CF_3SO_3^-$, $C_6H_5SO_3^-$, $CH_3C_6H_4SO_3^-$, $HOSO_3^-$, and $H_2PO_4^-$, the Mannich base is represented by any of the following general formulae (5) to (7):

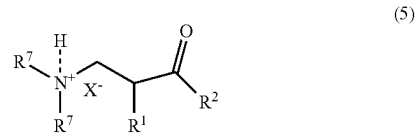

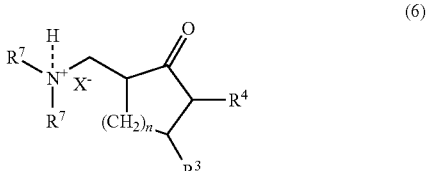

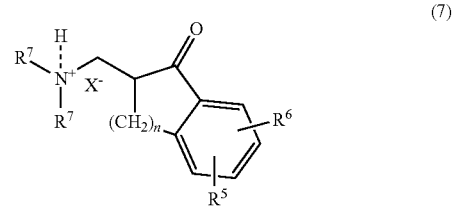

$R^1$, $R^2$, $R^3$, $R^4$, $R^5$, $R^6$, and n in the formulae (5) to (7) have the same meanings as those of $R^1$, $R^2$, $R^3$, $R^4$, $R^5$, $R^6$, and n in the formulae (1) to (3), and $R^7$ and $X^-$ in the formulae (5) to (7) have the same meanings as those of $R^7$ and $X^-$ in the formula (4); and a second step of reacting the Mannich base and a diene compound with each other by adding an organic solvent, a base in an amount of 1.0 to 20.0 equivalents to the acid, and the diene compound to the reaction liquid, and then heating the reaction liquid, to thereby form a norbornene derivative, wherein the diene compound is represented by the following general formula (8):

wherein the formula (8), $R^8$ represents any one selected from the group consisting of a hydrogen atom, linear chain saturated hydrocarbon groups having 1 to 10 carbon atoms, branched chain saturated hydrocarbon groups having 3 to 10 carbon atoms, and a fluorine atom, the norbornene derivative is represented by any of the following general formulae (9) to (11):

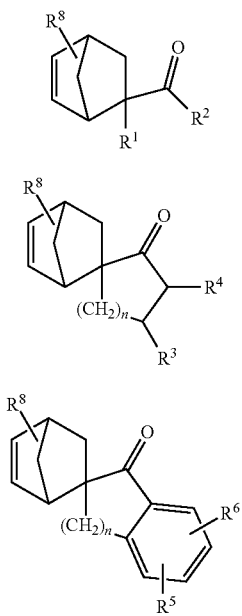

$R^1$, $R^2$, $R^3$, $R^4$, $R^5$, $R^6$, and n in the formulae (9) to (11) have the same meanings as those of $R^1$, $R^2$, $R^3$, $R^4$, $R^5$, $R^6$, and n in the formulae (1) to (3), and $R^8$ in the formulae (9) to (11) has the same meaning as that of $R^8$ in the formula (8).

2. The method for producing a norbornene derivative according to claim 1, wherein the acidic solvent comprises 0.01 to 2.0 mol/L of the acid.

3. The method for producing a norbornene derivative according to claim 1, wherein the base added to the reaction liquid is at least one selected from the group consisting of amines, alkali metal hydroxides, and alkaline earth metal hydroxides.

4. The method for producing a norbornene derivative according to claim 1, wherein the amount of the base added to the reaction liquid is 1.5 to 10.0 equivalents to the acid.

5. The method for producing a norbornene derivative according to claim 1, wherein a heating temperature in the second step is 60 to 180° C.

6. The method for producing a norbornene derivative according to claim 1, wherein, in the second step,
a content of the base is 2.0 to 5.0 equivalents to the acid comprised in the reaction liquid,
a heating temperature is 85 to 125° C., and a heating time is 0.5 to 1.5 hours.

7. The method for producing a norbornene derivative according to claim 1, wherein
the organic solvent added to the reaction liquid is an organic solvent immiscible with a saturated hydrocarbon having 3 to 30 carbon atoms, and
after a reaction, the norbornene derivative is liquid-liquid extracted directly from the reaction liquid with the saturated hydrocarbon having 3 to 30 carbon atoms.

8. The method for producing a norbornene derivative according to claim 1, comprising a step in which,
after the norbornene derivative is formed in the second step by using an organic solvent miscible with the saturated hydrocarbon having 3 to 30 carbon atoms as the organic solvent added to the reaction liquid, the organic solvent miscible with a saturated hydrocarbon having 3 to 30 carbon atoms is removed from the mixture liquid comprising the norbornene derivative, and then
while the mixture liquid from which the organic solvent is removed is used as it is or with water added to the mixture liquid, the norbornene derivative is separated by extraction with the saturated hydrocarbon having 3 to 30 carbon atoms.

9. The method for producing a norbornene derivative according to claim 7, further comprising, after the step of separation by extraction, a step of washing, with an aqueous alkaline solution and an aqueous acid solution, an extraction liquid comprising the norbornene derivative and the saturated hydrocarbon having 3 to 30 carbon atoms, the norbornene derivative being obtained by separating the norbornene derivative by extraction using the saturated hydrocarbon.

10. The method for producing a norbornene derivative according to claim 8, further comprising, after the step of separation by extraction, a step of washing, with an aqueous alkaline solution and an aqueous acid solution, an extraction liquid comprising the norbornene derivative and the saturated hydrocarbon having 3 to 30 carbon atoms, the norbornene derivative being obtained by separating the norbornene derivative by extraction using the saturated hydrocarbon.

* * * * *